US010286197B2

(12) United States Patent
Pouliot et al.

(10) Patent No.: US 10,286,197 B2
(45) Date of Patent: May 14, 2019

(54) PATIENT-SPECIFIC TEMPORARY IMPLANTS FOR ACCURATELY GUIDING LOCAL MEANS OF TUMOR CONTROL ALONG PATIENT-SPECIFIC INTERNAL CHANNELS TO TREAT CANCER

(71) Applicant: THE REGENTS OF THE UNIVERSITY OF CALIFORNIA, Oakland, CA (US)

(72) Inventors: Jean Pouliot, Mill Valley, CA (US); Ken Goldberg, Mill Valley, CA (US); I-Chow Hsu, San Francisco, CA (US); J. Adam M. Cunha, San Bruno, CA (US); Animesh Garg, Berkeley, CA (US); Sachin Patil, Berkeley, CA (US); Pieter Abbeel, Berkeley, CA (US); Timmy Siauw, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 216 days.

(21) Appl. No.: 14/907,679

(22) PCT Filed: Jul. 28, 2014

(86) PCT No.: PCT/US2014/048488
§ 371 (c)(1),
(2) Date: Jan. 26, 2016

(87) PCT Pub. No.: WO2015/013716
PCT Pub. Date: Jan. 29, 2015

(65) Prior Publication Data
US 2016/0271379 A1 Sep. 22, 2016

Related U.S. Application Data

(60) Provisional application No. 61/859,096, filed on Jul. 26, 2013, provisional application No. 61/859,687, filed on Jul. 29, 2013.

(51) Int. Cl.
*A61M 31/00* (2006.01)
*A61B 8/08* (2006.01)
(Continued)

(52) U.S. Cl.
CPC .......... *A61M 31/002* (2013.01); *A61B 6/032* (2013.01); *A61B 6/037* (2013.01); *A61B 8/085* (2013.01);
(Continued)

(58) Field of Classification Search
CPC .......... A61B 18/14; A61B 2018/00559; A61B 2018/00577; A61B 2018/00791;
(Continued)

(56) References Cited

U.S. PATENT DOCUMENTS 5,339,223 A 8/1994 Kremenchugsky et al.
5,400,425 A 3/1995 Nicholas et al.
(Continued)

OTHER PUBLICATIONS

Albano, et al., *Cancer Ra-diother*, 12:822-6, 2008.
(Continued)

*Primary Examiner* — Christine H Matthews
*Assistant Examiner* — Joshua Daryl D Lannu
(74) *Attorney, Agent, or Firm* — Morgan, Lewis & Bockius LLP; Jeffry S. Mann; Todd Esker

(57) ABSTRACT

The present invention offers an alternative for cancer treatment where radiation, thermotherapy, or another therapeutic modality must be delivered to an internal cavity of a subject, for example to treat mouth, anal, cervical, and vaginal cancers. The invention is a new approach that builds on recent results in 3D printing and steerable needle motion planning to create customized implants containing customized curvature-constrained internal channels that fit securely, minimize air gaps, and precisely guide treatment sources
(Continued)

through internal printed channels to accurately reach tumors and minimize damage to healthy tissue.

36 Claims, 49 Drawing Sheets

(51) Int. Cl.

| | |
|---|---|
| A61B 6/03 | (2006.01) |
| A61N 5/06 | (2006.01) |
| A61N 5/10 | (2006.01) |
| A61N 7/02 | (2006.01) |
| A61B 18/18 | (2006.01) |
| A61B 18/14 | (2006.01) |
| A61B 18/00 | (2006.01) |
| A61B 18/02 | (2006.01) |
| B33Y 10/00 | (2015.01) |
| B33Y 80/00 | (2015.01) |
| A61B 90/00 | (2016.01) |
| A61F 7/12 | (2006.01) |
| B29K 101/12 | (2006.01) |
| B29L 31/00 | (2006.01) |
| B29C 64/112 | (2017.01) |
| B29C 64/20 | (2017.01) |

(52) U.S. Cl.
CPC ........ *A61B 18/1815* (2013.01); *A61N 5/0603* (2013.01); *A61N 5/1014* (2013.01); *A61N 7/022* (2013.01); *A61B 18/14* (2013.01); *A61B 2018/00559* (2013.01); *A61B 2018/00577* (2013.01); *A61B 2018/00791* (2013.01); *A61B 2018/0212* (2013.01); *A61B 2018/1861* (2013.01); *A61B 2090/3983* (2016.02); *A61F 2007/126* (2013.01); *A61M 2207/00* (2013.01); *A61N 5/062* (2013.01); *A61N 5/1016* (2013.01); *A61N 5/1049* (2013.01); *A61N 2005/0606* (2013.01); *A61N 2005/0608* (2013.01); *A61N 2005/0611* (2013.01); *A61N 2005/1018* (2013.01); *A61N 2005/1094* (2013.01); *B29C 64/112* (2017.08); *B29C 64/20* (2017.08); *B29K 2101/12* (2013.01); *B29K 2995/0056* (2013.01); *B29L 2031/753* (2013.01); *B33Y 10/00* (2014.12); *B33Y 80/00* (2014.12)

(58) Field of Classification Search
CPC ........ A61B 2018/0212; A61B 18/1815; A61B 2018/1861; A61B 6/037; A61B 6/032; A61B 2090/3983; A61B 8/085; A61N 5/0603; A61N 5/062; A61N 5/1014; A61N 5/1016; A61N 5/1049; A61N 7/022; A61N 2005/0606; A61N 2005/0608; A61N 2005/0611; A61N 2005/1018; A61N 2005/1094; A61M 2207/00; A61M 31/002; A61F 2007/126; B29K 2101/12; B29K 2995/0056; B29C 67/0085; B29C 67/0059; B29L 2031/753; B33Y 80/00; B33Y 10/00
See application file for complete search history.

(56) References Cited

U.S. PATENT DOCUMENTS

| | | |
|---|---|---|
| 5,792,214 A | 8/1998 | Larsson et al. |
| 6,045,575 A | 4/2000 | Rosen et al. |
| 6,290,713 B1 | 9/2001 | Russell |
| 6,596,016 B1 | 7/2003 | Vremen et al. |
| 6,872,220 B2 | 3/2005 | Williams et al. |
| 2004/0039428 A1 | 2/2004 | Williams et al. |
| 2004/0068305 A1 | 4/2004 | Bansal et al. |
| 2006/0100675 A1 | 5/2006 | Gardner |
| 2006/0116546 A1* | 6/2006 | Eng ................. A61N 5/1016 600/3 |
| 2007/0276501 A1 | 11/2007 | Betz et al. |
| 2011/0160587 A1 | 6/2011 | Nycz et al. |
| 2012/0109304 A1* | 5/2012 | Balckwell .......... A61B 17/7061 623/17.12 |
| 2013/0238096 A1 | 9/2013 | Kotlus |

OTHER PUBLICATIONS

Anchieta, et al., *Advanced Applications of Rapid Prototyping Technology in Modern Engineering*. Rijeka, Croatia: InTech, pp. 153-172, 2011.
Bernstein et al., "Results of the Hybrid Interstitial-Intracavitary Utrecht Aapplicator for cervical cancer in an Outpatient setting," Radiotherapy and Oncology, 103:S116, 2012.
Borg and Rogers, "Monte carlo calculations of photon spectra in air from $^{192}$Ir sources," National Research Council Report PIRS-629r, Ontario, Canada, 1999.
Chow, et al., *Journal of Oral and Maxillofacial Surgery*, 65(11):2260-2268, 2007.
Cohen, et al., *Oral Surgery, Oral Medicine, Oral Pathology, Oral Radiology, and Endodontology*, 108(5):661-666, 2009.
Cowan et al., "Robotic needle steering: Design, modeling, planning, and image guidance," in *Surgical Robotics: System Applications and Visions* (J. Rosen, B. Hannaford, and R. M. Satava, eds.), ch. 23, pp. 557-582, Springer, 2011.
Delclos et al., "Minicolpostats, dome cylinders, other additions and improvements of the Fletcher-Suit afterloadable system: Indications and limitations of their use," International Journal of Radiation Oncology Biology Physics, 6(9):1195-1206, 1980.
D'haese et al., "Accuracy and complications using computer-designed stere¬olithographic surgical guides for oral rehabilitation by means of dental implants: a review of the literature," Clinical implant dentistry and related research, 14:321-35, 2012.
Dimopoulos et al., "The Vienna applicator for combined intracavitary and interstitial brachytherapy of cervical cancer: Clinical feasibility and preliminary results," International Journal of Radiation Oncology Biology Physics, 66(1):83-90, 2006.
Garg et al., "Initial experiments toward au¬tomated robotic implantation of skew-line needle arrangements for {HDR} brachytherapy," in Automation Science and Engineering (CASE), 2012 IEEE International Conference on, pp. 26-33, 2012.
Garg et al., "An Algorithm for Computing Customized 3D Printed Implants with Curvature Constrained Channels for Enhancing Intracavitary Brachytherapy Radiation Delivery." Accepted for publication in *IEEE International Conference on in Automation Science and Engineering (CASE)*, IEEE, 2013.
Huang and Low, "Comprehensive planning of robotic therapy and assessment of task-oriented functions via improved {QFD} applicable to hand rehabilitation," in Automation Science and Engineering (CASE), IEEE Conference on, pp. 252-257, 2010.
Koo, et al., *The International Journal of Artificial Organs*, 33(10):731, 2010.
Maalej, et al., *Cancer/Radiotherapie*, 11(3):117-121, 2007.
Magne et al., "Technical aspects and perspectives of the vaginal mold applicator for brachytherapy of gynecologic malignancies," Brachytherapy, 9(3):274-277, 2010.
Makni, et al., *Prostate Cancer Imaging. Image Analysis and Image-Guided Interventions*, pp. 22-34, 2011.
Melchels et al., "A review on stereolithography and its applications in biomedical engineering." Biomaterials, 31:6121-30, 2010.
Mendez et al., "Model-based controller for anesthesia automation," in 2009 IEEE International Conference on Automation Science and Engineering, pp. 379-384, 2009.
Mutic, et al., *International Journal of Radiation Oncology Biology Physics*, 52(4):1104-1110, 2002.
Novakova-Marcincinova, et al., Advanced Materials Research, 740:597-602, 2013.

(56) References Cited

OTHER PUBLICATIONS

Ny et al., "On the Dubins Traveling Salesman Problem," *IEEE Transactions on Automatic Control*, 57:265-270, 2012.

Patil and Alterovitz, "Interactive Motion Planning for Steerable Needles in 3D Environments with Obstacles.," *Proceedings of the . . . IEEE/RAS-EMBS International Conference on Biomedical Robotics and Biomechatronics.* pp. 893-899, 2010.

Pompeu-Robinson, et al., *International Journal of Computer Assisted Radiology and Surgery*, 7(1):65-72, 2012.

Pötter, et al., "Recommendations from gynaecological (GYN) GEC ESTRO working group (II): Concepts and terms in 3D image-based treatment planning in cervix cancer brachytherap 3D dose volume parameters and," Radiotherapy and Oncology, 78(1):67-77, 2006.

Pötter et al., "Upcoming ICRU/GEC ESTRO recommendations for brachytherapy in cancer of the Cervix (1)," Radiotherapy and Oncology, 103:S42, 2012.

Poulsen, et al., *International Journal of Radiation Oncology Biology Physics*, 44(3):731-735, 1999.

Roy et al. "CT-based optimized planning for transperineal prostate implant with customized template," *International Journal of Radiation Oncology Biology Physics*, 21:483-489, 1991.

Seitz et al., "Three-dimensional printing of porous ceramic scaffolds for bone tissue engineering." Journal of biomedical materials research. Part B, Applied biomaterials, 74:782-8, 2005.

Schrank, et al., Journal of Biomechanical Engineering, 135(1):101011, 2013.

Solis et al., "Towards enhancing the understanding of human motor learning," International Conference on Automation Science and Engineering, pp. 591-596, IEEE, Aug. 2009.

Subburaj et al., "Automated 3D geometric reasoning in Computer Assisted joint reconstructive surgery," in 2009 IEEE International Conference on Automation Science and Engineering, pp. 367-372, 2009.

Winder, et al., *Journal of Oral and Maxillofacial Surgery: Official Journal of the American Association of Oral and Maxillofacial Surgeons*, 63(7):1006, 2005.

Winder, et al., *Journal of Medical Engineering & Technology*, 23(1):26-28, 1999.

Tervo et al. "Skill Evaluation of Human Operators in Partly Automated Mobile Working Machines," IEEE Transactions on Automation Science and Engineering, 7:133-142, 2010.

Xu et al., "Motion planning for steerable needles in 3D environments with obstacles using rapidly-exploring Random Trees and backchaining," in 2008 IEEE International Conference on Automation Science and Engineering, pp. 41-46, IEEE, 2008.

* cited by examiner

FIG. 4
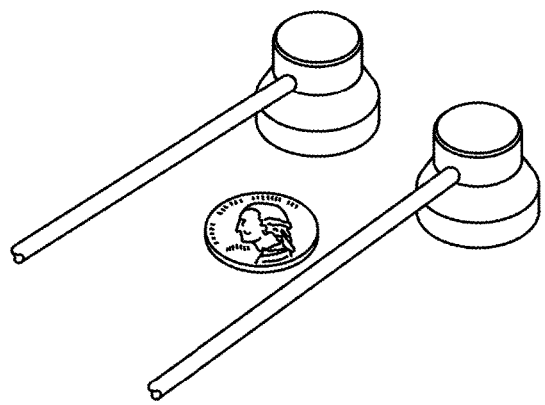
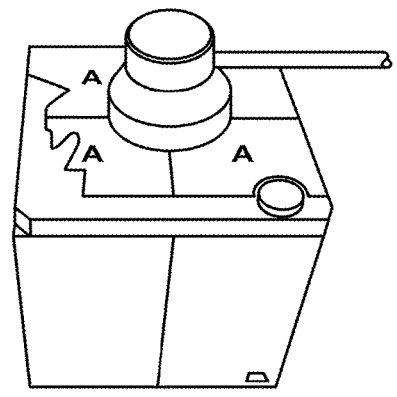
(a)            (b)
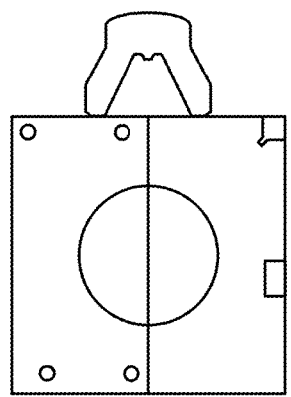
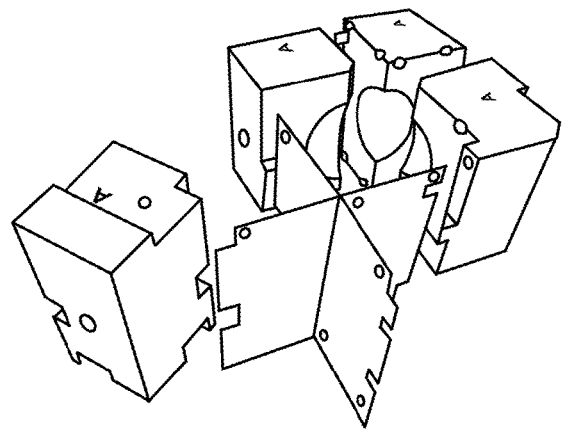
(c)            (d)

FIG. 12

```
Algorithm 1 C ← channel_layout(I, E, T, r_min, w)
 1: D ← generate_dwell_segments(I, T)
 2: C = ∅
 3: for all d ∈ D do
 4:     X ← ∅
 5:     X ← add_vertex(X_d)
 6:     repeat
 7:         p_rand ← random_point_in_R³(I, C)
 8:         X_near ← nearest_neighbor(p_rand, X, r_min)
 9:         X_new ← circular_arc(X_near, p_rand)
10:         if collision_free(X_near, X_new, I, C) then
11:             X ← add_vertex(X_new)
12:             X ← add_edge(X_near, X_new)
13:         end if
14:     until ((p_new ∈ E) ∧ permissible(R_new))
15:     C_d ← build_channel(X, X_new, w)
16:     C ← C ∪ C_d
17: end for
18: return C
```

PATIENT-SPECIFIC TEMPORARY IMPLANTS FOR ACCURATELY GUIDING LOCAL MEANS OF TUMOR CONTROL ALONG PATIENT-SPECIFIC INTERNAL CHANNELS TO TREAT CANCER

CROSS-REFERENCE TO RELATED APPLICATIONS

This application claims under 35 USC 119(e) the benefit of U.S. Provisional Application No. 61/859,096, filed Jul. 26, 2013, and U.S. Provisional Application No. 61/859,687 filed Jul. 29, 2013, each of which is incorporated herein by reference in its entirety for all purposes.

STATEMENT AS TO RIGHTS TO INVENTIONS MADE UNDER FEDERALLY SPONSORED RESEARCH OR DEVELOPMENT

This invention was made with Government support under Grant No. 0905344 and Grant No. IIS-1227536 awarded by the NSF. The Government has certain rights in the invention.

FIELD OF THE INVENTION

The technology relates generally to the focused delivery of therapy such as phytotherapy, cryosurgery, thermotherapy, radiation therapy, and chemotherapy to regions of diseased tissue as exemplified by devices for brachytherapy and methods of using and making such devices.

The present invention offers an alternative for cases where radiation, thermotherapy, or another therapeutic modality must be delivered to an internal cavity of a subject, for example to treat mouth, anal, cervical, and vaginal cancers, and can also be used in the rectum to treat prostate cancers.

BACKGROUND OF THE INVENTION

Worldwide, more than 10 million people are diagnosed with cancer every year and it is estimated that this number will grow to 15 million new cases every year by 2020. Cancer causes six million deaths every year or 12% of the deaths worldwide. There remains a need for methods that can treat cancer in a localized manner, thereby avoiding excessive toxicity or damage to non-cancerous tissues proximate to the cancerous tissue and to minimize the effects of systemic toxicity of agents by localizing the delivery of these agents. The present invention provides devices and methods to meet these needs.

Cancer can develop in any tissue of any organ at any age. The etiology of cancer is not clearly defined but mechanisms such as genetic susceptibility, chromosome breakage disorders, viruses, environmental factors and immunologic disorders have all been linked to a malignant cell growth and transformation. Cancer encompasses a large category of medical conditions, affecting millions of individuals worldwide. Cancer cells can arise in almost any organ and/or tissue of the body. Cancer develops when cells in a part of the body begin to grow or differentiate out of control. All cancer types begin with the out-of-control growth of abnormal cells.

There are many types of cancer, including, breast, lung, ovarian, bladder, prostate, pancreatic, cervical, and leukemia. Currently, some of the main treatments available are surgery, phototherapy, phytotherapy, cryosurgery, thermotherapy, radiation therapy, and chemotherapy.

Cryosurgery, or the destruction of undesired biological tissues by freezing, has long been accepted as an important alternative technique of surgery. Compared with conventional means of destroying tissues, such as surgical excision, radiotherapy and chemotherapy, visceral cryosurgery (especially minimal-invasive cryosurgery) offers the following potential advantages: simplicity of the procedure, minimal bleeding, anaesthetic effect of low temperatures, short period of patient recovery, low cost, minimal scarring, and possible stimulation of the body's immune system. Exemplary cryosurgery devices are described in Rabin et al., U.S. Pat. No. 5,899,897.

Thermotherapy treatment is a relatively new method of treating diseased and/or undesirably enlarged human tissues, e.g., prostate tissues. Hyperthermia treatment is well known in the art, involving the maintaining of a temperature between about 41.5° through 45° C. Thermotherapy, on the other hand, usually requires energy application to achieve a temperature above 45° C. for the purposes of coagulating the target tissue. Tissue coagulation beneficially changes the density of the tissue. As the tissue shrinks, forms scars and is reabsorbed, the impingement of the enlarged tissues, such as an abnormal prostate, is substantially lessened.

The higher temperatures required by thermotherapy require delivery of large amounts of energy to the target tissues. At the same time, it is important to shield nontarget tissues from the high thermotherapy temperatures used in the treatment. Providing safe and effective thermotherapy, therefore, requires devices which have further capability to direct heat to a desired region compared to those which are suitable for hyperthermia.

Phototherapy is a promising clinical tool for the treatment for many conditions, including, but not limited to, cancer. Exemplary phototherapy systems are described, e.g., in Kremenchugsky U.S. Pat. No. 5,339,223; Rosen U.S. Pat. No. 6,045,575; Russell U.S. Pat. No. 6,290,713; Larsson U.S. Pat. No. 5,792,214; Nicholas U.S. Pat. No. 5,400,425; Vreman U.S. Pat. No. 6,596,016; Williams U.S. Pat. No. 6,872,220; Williams U.S. Pub. No. 2004/0039428; Bansal U.S. Pub. No. 2004/0068305; and Gardner U.S. Pub. No. 2006/0100675.

Regardless of the technique used, it is important to limit the "leakage" of phototherapeutic light; that is, phototherapeutic light absorbed by non-cancerous tissue. Ideally, all the emitted light is absorbed by the locus of disease, however a significant percentage of the phototherapeutic light never strikes the locus of disease. Systems and devices are therefore needed focus the light during phototherapy.

Chemotherapy involves the administration of various anti-cancer drugs to a patient but due to the requirement that it be administered systemically, its use is accompanied by adverse side effects. Thus, devices and methods for delivering chemo-therapeutic agents to desired regions of disease are needed.

A fundamental goal for radiation oncology is precise delivery of radiation to tumors while sparing healthy tissue. It is critical to minimize the exposure of non-cancerous tissue to ionizing radiation during radiation therapy. Methods employing beams of photons or other sub-atomic or atomic particles generated outside the body and penetrating into the body and tumor location (external beam) can accumulate radiation at specific internal points, but radiation intensity is limited by the dose delivered to intervening non-cancerous tissue. In contrast, brachytherapy (a form of radiotherapy where needles are inserted into the body to place small radioactive sources near tumors) can place high-intensity radiation inside the body, circumventing the intervening non-cancerous tissue. Each year, over 500,000 cancer patients worldwide are treated with brachytherapy.

A problem with needles is that they are difficult to place precisely, their paths are limited to primarily linear forms, and that radiation is emitted uniformly in all directions when the seed is stationary. FIG. 10 displays representative conventional brachytherapy devices.

There remains a need for methods that can treat cancer and other diseases in a localized manner, thereby avoiding excessive toxicity or damage to non-cancerous tissues proximate to the cancerous tissue and, in the case of chemotherapy, to minimize the effects of systemic toxicity of chemotherapeutic agents by localizing the delivery of these agents. The present invention provides devices and methods to meet these needs.

BRIEF SUMMARY OF THE INVENTION

The present invention offers an alternative for cases where radiation, thermotherapy, or another therapeutic modality must be delivered to internal cavities, for example to treat mouth, anal, cervical, and vaginal cancers. In various embodiments, the invention is a new approach that builds on recent results in 3D printing and steerable needle motion planning to create customized implants containing customized curvature-constrained internal channels that fit securely, minimize air gaps, and precisely guide treatment sources through internal printed channels to accurately reach tumors and minimize damage to healthy tissue.

In an exemplary embodiment the invention provides a removeably implantable device customized to contact an internal surface of a body cavity of a subject in which said device is implanted. An exemplary device is configured to provide localization of at least one tissue-ablating means to a diseased tissue of the subject. The diseased tissue is located on the surface of the body cavity, or interstitially with the body cavity providing proximal access, and is contacted by the device or it is sufficiently proximate to the body cavity that the device delivers a therapeutically effective dose of the local means of tumor control to the diseased tissue. An exemplary device includes: a device body with an exterior surface configured to contact at least a portion of the internal surface of the body cavity, and defined by the exterior surface is an internal region having at least one curvature-constrained channel disposed therein. The channel includes at least one opening communicating with the external surface. In various embodiments, the channel has two openings, each communicating with a different zone of the exterior surface of the device. An exemplary device of the invention also includes at least one local means of tumor control disposed within at least one curvature constrained channel.

Also provided is a method for treating diseased tissue in a patient in need of such treatment. An exemplary method of the invention includes implanting a device of the invention in a body cavity of said subject. The body cavity either includes the region of diseased tissue or is sufficiently proximate to the diseased tissue that the implanted device delivers a therapeutically effective dose of the local means of tumor control to the diseased tissue. In an exemplary embodiment, the diseased tissue is a neoplastic disease and the therapeutically effective dose of the local means of tumor control is delivered to a locus of the neoplastic disease, e.g., a tumor. In various embodiments, the local means of tumor control is ionizing radiation and it is delivered to the diseased tissue from a dwell point in the device. The source of radiation is optionally removeable from the device.

The invention also provides methods of making a device of the invention. An exemplary method includes printing the device using additive manufacture, also referred to as 3-dimensional printing (3D printing). In various embodiments, a 3-dimensional model of the body cavity is produced and the device is 3-dimensionally printed from a digitized scan of the model.

An exemplary method of the invention utilizes imaging technologies such as ultrasound (US), computed tomography (CT), or magnetic resonance imaging (MRI) to scan patient anatomy and localize cancers. The method uses additive manufacturing technologies such as 3D printing to fabricate precise implants with external geometry matching the internal geometry of the patient cavity, with precise and not necessarily linear internal channels for the radioactive source (or thermotherapy source, for example) to be moved through, and in a preferred embodiment to create or print additional channels for radioactive shielding such as lead that can shape the radiation field along desired directions along the paths.

Other objects, advantages and embodiments of the invention are illustrated by the detailed description that follows.

BRIEF DESCRIPTION OF THE DRAWINGS

FIG. 2 is a case study for OB/GYN cancer. Left: 3D model of customized implant for treating tumors of the cervix and endometrium of the vaginal cavity. The left figure shows an anatomical configuration of the vaginal canal (roughly cylindrical, transparent orange) with the cervix at the distal end (top of figure) and vaginal opening at the bottom of the figure. Five tumors, one around the cervix (top) and four on the vaginal sidewall, are depicted. Right: Customized implant with 12 curvature constrained channels (in light blue) generated by the algorithm. The small radioactive source (seed, see FIG. 11) can be precisely guided through each channel by a wire (controlled by a programmable afterloader) sequentially from each entry point (bottom) to each dwell segment (in solid blue) to precisely deliver treatment to the tumors.

FIG. 4 is a 3D printed replica of a Leipzig applicator generally used for skin irradiation, but used here for mouse irradiation. (a) Right: titanium Leipzig applicator sold by Elekta. Left: 3D-printed disposable replica of the Elekta applicator. (b) and (d) Dosimetry characterization of the 3D-printed devices is performed using radio-sensitive film sandwiched between water-density-mimicking solid material. (c) A CT image of the applicator situated on the film cube.

FIG. 12 is an Algorithm table generated in a method of the invention.

DETAILED DESCRIPTION OF THE INVENTION

I. Introduction

The present invention is illustrated by reference to an embodiment in which the device of the invention is designed for brachytherapy. As will be appreciated by those of skill in the art, this focus is purely for purposes of illustration and does not limit the scope of the device of the invention, which finds use in other treatment modalities including, but not limited to cryosurgery, thermal therapy, phototherapy, chemotherapy and the like.

Figure 10:
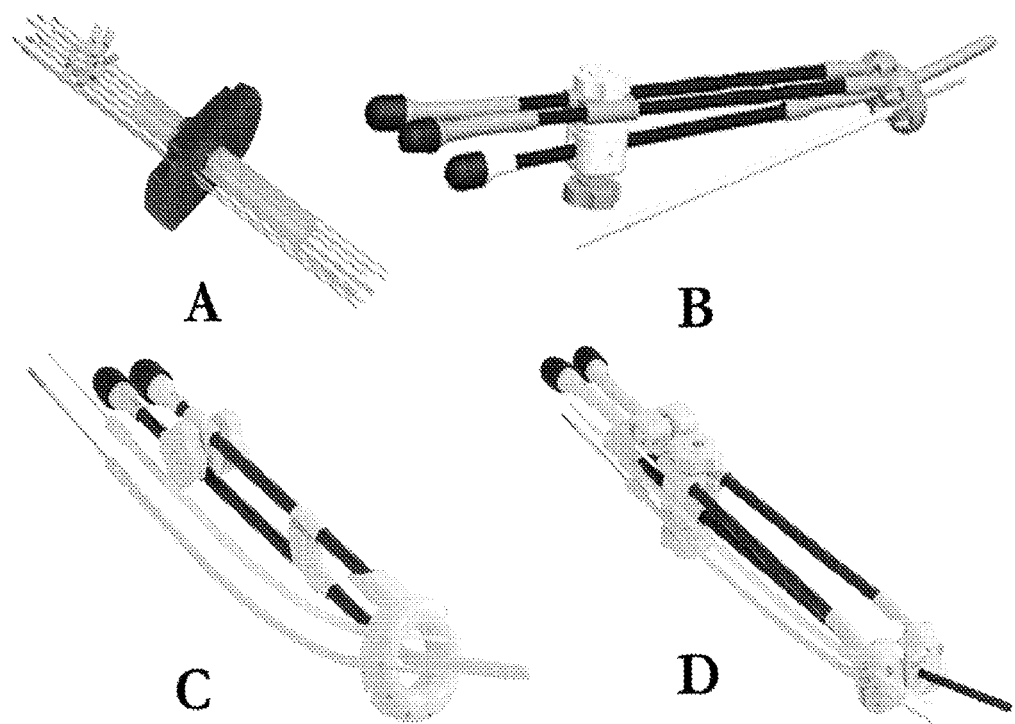
FIGS. 10A, 10B, 10C and 10D are standardized templates/applicators/implants commercially available for gynecological brachytherapy. (A) Vaginal cylinder applicator with 8 parallel catheters, (B & D) Ovoids applicator with interstitial channels and uterine tandem applicator, (C) Ring applicator with interstitial channels and uterine tandem applicator. The uterine tandem applicator provides a channel for dwell positions along the uterine canal. The interstitial channels allow for applicator-guided insertion of catheters into the tissue surrounding the cervix.
Figure 11:
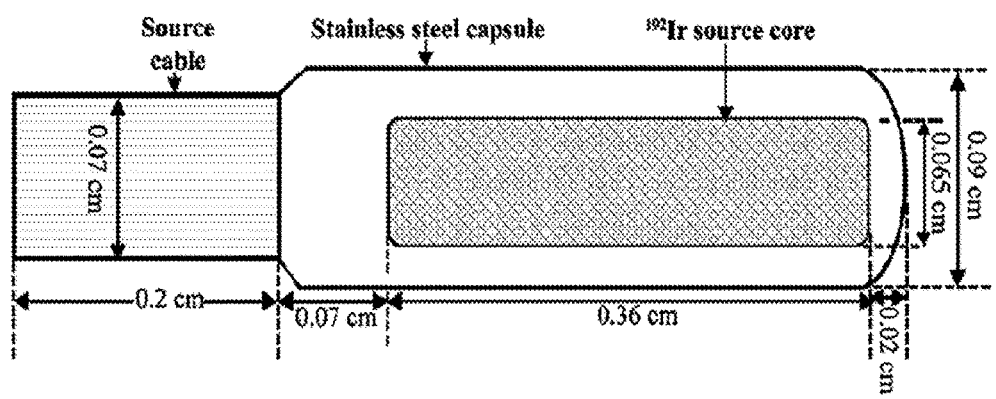
FIG. 11 is a schematic of a typical $^{192}$Ir source used in high dose rate brachytherapy for many tumor locations (e.g. cervix, prostate, breast, tongue, anus, etc.).
Figure 14:
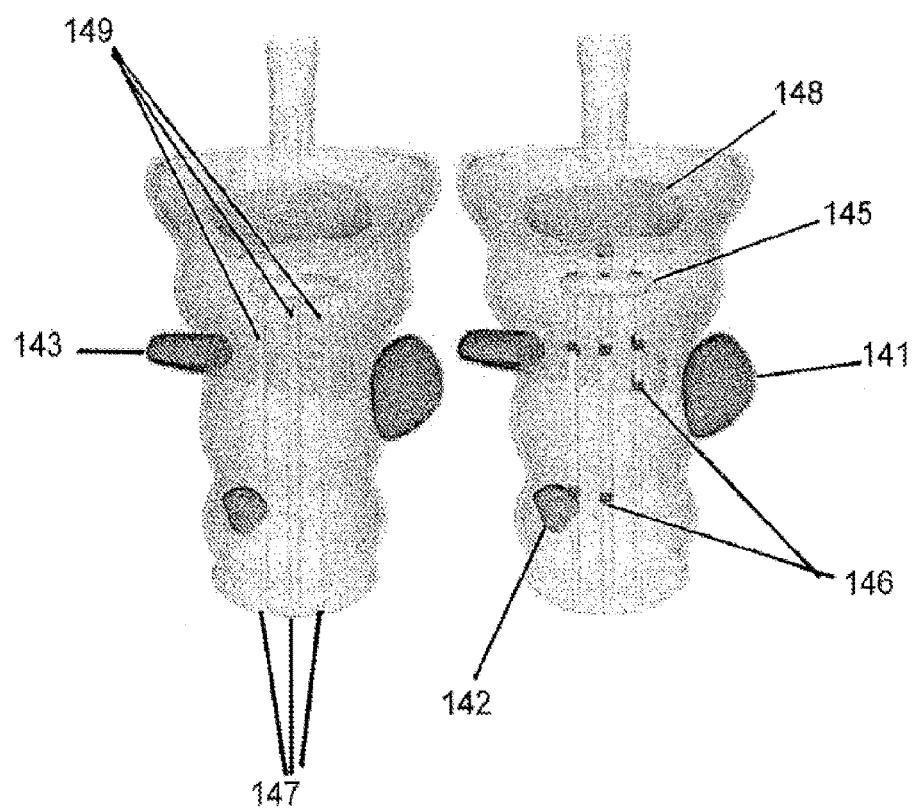
FIG. 14 is a standardized ring implant (Left FIG.) in which the channels providing access to the proximity of the tumor for the radioactive source cannot conform to patient anatomy. Only 18 dwell positions are reachable (Right FIG.).

Brachytherapy is radiation therapy in which the source of radiation is placed in or close to the area to be treated, such as within a cavity or void left after surgical resection of a tumor. Brachytherapy may be administered by implanting or delivering a spatially confined radioactive material to a treatment site, which may be a cavity left after surgical resection of a tumor. For example, brachytherapy may be performed by using an implantable device (e.g., catheter or applicator) to implant or deliver radiation sources directly into the tissue(s) or cavity to be treated. During brachytherapy treatment, a catheter may be inserted into the body at or near the treatment site and subsequently a radiation source may be inserted through the catheter and placed at the treatment site. FIG. 10 and FIG. 14 display conventional brachytherapy devices. FIG. 14 shows a standardized ring implant, which cannot conform to patient anatomy and has only 18 accessible dwell points. FIG. 14 depicts a brachytherapy device in current use as it is situated in the patient for treatment. In contrast, FIG. 16 displays a 3-D printed implant designed with linear channels into which a source of ionizing radiation is installed. 164 and 169 are the internal and exterior surfaces of the device, respectively. Linear channels 165 are disposed within the body of the device and include openings 167 to the exterior surface of the device. The sources of ionizing radiation, 166 are located proximate to regions of neoplastic tissue 161, 162, 163 and 168.

Brachytherapy is typically most appropriate where: (1) malignant tumor regrowth occurs locally, within 2 or 3 cm of the original boundary of the primary tumor site; (2) radiation therapy is a proven treatment for controlling the growth of the malignant tumor; and (3) there is a radiation dose-response relationship for the malignant tumor. But, the dose that can be given safely with conventional external beam radiotherapy is limited by the tolerance of normal tissue. Interstitial and/or intercavity brachytherapy may be useful for treating malignant brain and breast tumors, among other types of proliferative tissue disorders.

There are two basic types of brachytherapy, high dose rate and low dose rate. These types of brachytherapy generally include the implantation of radioactive seeds such as palladium or iodine, into the tumor, organ tissues, or cavity to be treated. Low dose rate (LDR) brachytherapy often refers to implantation of multiple seeds into the patient's body via needles. These sources are left in place permanently. High dose rate brachytherapy (HDR) uses catheters or applicators, to bring a radioactive seed in close proximity of the tumor for a treatment period of the order of minutes, after which both the sources and applicators are removed. Typically, only a single radiation source is used, but of very high strength. This single source is remotely positioned within the applicators at one or more positions, for treatment times which are measured in seconds to minutes. The treatment may be divided into multiple sessions ('fractions'), which are repeated over a course of a few days. In particular, an applicator (also referred to as an applicator catheter or treatment catheter) is inserted at the treatment site so that the distal region is located at the treatment site while the proximal end of the applicator protrudes outside the body. The proximal end is connected to a transfer tube, which in turn is connected to an afterloader to create a closed transfer pathway for the radiation source to traverse from its shielded containment device to the patient. Once the closed pathway is complete, the afterloader directs its radioactive source (which is attached to the end of a wire controlled by the afterloader) through the transfer tube into the treatment applicator for a set amount of time. When the treatment is completed, the radiation source is retracted back into the afterloader, and the transfer tube is disconnected from the applicator.

The dose rate at a target point exterior to a radiation source is inversely proportional to the square of the distance between the radiation source and the target point. Thus, previously described applicators, such as those described in U.S. Pat. No. 6,482,142, issued on Nov. 19, 2002, to Winkler et al., are symmetrically disposed about the axis of the tubular member so that they position the tissue surrounding the balloon at a uniform or symmetric distance from the axis of the tubular member. In this way, (for this particular applicator), the radiation dose profile from a radiation source placed within the tubular member at the location of the balloon is symmetrically shaped relative to the balloon. In general, the amount of radiation desired by a treating physician is a certain minimum amount that is delivered to a region up to about two centimeters away from the wall of the excised tumor, i.e., the target treatment region. It is desirable to keep the radiation that is delivered to the tissue in this target tissue within a narrow absorbed dose range to prevent over-exposure to tissue at or near the balloon wall, while still delivering the minimum prescribed dose at the maximum prescribed distance from the balloon wall (i.e., the two centimeter thickness surrounding the wall of the excised tumor).

However, in some situations, such as a treatment site located near sensitive tissue like a patient's skin, the symmetric dosing profile may provide too much radiation to the sensitive tissue such that the tissue suffers damage or even necrosis. In such situations, the dosing profile may cause unnecessary radiation exposure to healthy tissue or it may damage sensitive tissue, or it may not even be possible to perform a conventional brachytherapy procedure.

The present invention solves these and other problems.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

In describing the present invention, the following terms will be employed, and are defined as indicated below.

II. Definitions

"Local means of tumor control" refers to a therapeutic modality delivered to a tumor by a device of the invention, which slows or arrests tumor growth and/or development. An exemplary local means of tumor control is a tissue ablating means. Exemplary tissue ablating means include, ionizing radiation, heat, cold, light and chemical agents.

"Tissue ablating means" refers to chemicals and forms of energy that are cytotoxic towards a category of tissue within the body of a subject, which is identified as diseased. Exemplary tissue ablation means include, heat, light, chemical toxins, ionizing radiation, and cold. Heat can be delivered by devices for and methods of heating tissue, e.g., thermotherapy, known in the art. Light can be delivered by devices for and methods of illuminating tissue, e.g., phototherapy, or photodynamic therapy, known in the art. Chemical toxins can be any of a wide variety of recognized chemotherapeutic agents including, without limitation, alkylating agents, antimetabolites, alkaloids and terpenoids, taxanes, topoisomerase inhibitors, and cytotoxic antibiotics. Heat can be removed from a region of diseased tissue by devices and methods recognized in the art, e.g., cryosurgery, using a gas, e.g., liquid nitrogen, argon, carbon dioxide, dimethyl ether-propane, or a cooling device. Ionizing radiation can be delivered to a region of diseased tissue using sources of radiation recognized in the art and known to be of use in brachytherapy. The device of the invention is configured to deliver to the diseased tissue one or more tissue ablating means.

"Cryosurgery" (cryotherapy) is the application of extreme cold to destroy abnormal or diseased tissue. Cryosurgery is used to treat a number of diseases and disorders, especially a variety of benign and malignant skin conditions and several internal disorders, including liver cancer, prostate cancer, lung cancer, oral cancers, cervical disorders and, more commonly in the past, hemorrhoids. Sources of cold of use for cryotherapy include, without limitation, liquid nitrogen, carbon dioxide, dimethyl ether-propane and argon. Recent advances in technology have allowed for the use of argon gas to drive ice formation using a principle known as the Joule-Thomson effect, using the identically named heat exchanger. This gives physicians excellent control of the ice, and minimizes complications.

The phrase "Joule-Thomson heat exchanger" refers, in general, to any device used for cryogenic cooling or for heating, in which a gas is passed from a first region of the device, wherein it is held under higher pressure, to a second region of the device, wherein it is enabled to expand to lower pressure. A Joule-Thomson heat exchanger may be a simple conduit, or it may include an orifice through which gas passes from the first, higher pressure, region of the device to the second, lower pressure, region of the device. It may further include a heat-exchanging configuration, for example a heat-exchanging configuration used to cool gasses from the first region of the device, prior to their expansion into the second region of the device. The expansion of certain gasses (referred to herein as "cooling gases") in a Joule-Thomson heat exchanger, when passing from a region of higher pressure to a region of lower pressure, causes these gasses to cool and may cause them to liquefy, creating a cryogenic pool of liquefied gas. This process cools the Joule-Thomson heat exchanger itself, and also cools any thermally conductive materials in contact therewith. As further described hereinbelow, the expansion of certain other gasses (referred to herein as "heating gasses") in a Joule Thompson heat exchanger causes the gas to heat, thereby heating the Joule-Thomson heat exchanger itself and also heating any thermally conductive materials in contact therewith.

The phrase "heat-exchanging configuration" is used herein to refer to component configurations traditionally known as "heat exchangers", namely configurations of components situated in such a manner as to facilitate the passage of heat from one component to another. Examples of "heat-exchanging configurations" of components include a porous matrix used to facilitate heat exchange between components, a structure integrating a tunnel within a porous matrix, a structure including a coiled conduit within a porous matrix, a structure including a first conduit coiled around a second conduit, a structure including one conduit within another conduit, or any similar structure.

"Photodynamic therapy" ("PDT") refers to a form of phototherapy using nontoxic or minimally toxic light-sensitive compounds that are exposed selectively to light, whereupon they become toxic to targeted malignant and other diseased cells. Photodynamic therapy is of use in treating. The FDA has approved the use of PDT to treat or relieve the symptoms of esophageal cancer and non-small cell lung cancer. In 2003, the FDA approved PDT in the treatment of precancerous lesions in patients with Barrett esophagus, a condition that can lead to esophageal cancer. Presently there is a wide range of coherent and non-coherent sources that can be used including, for example, dye lasers pumped by argon or metal vapor lasers frequency-doubled Nd:YAG lasers and femtosecond lasers. Non-laser sources include tungsten filament, xenon arc, metal halide, fluorescent lamps and LEDs.

"Thermosurgery" and "thermaltherapy" generate heat within tissue. Abnormal and diseased cells cannot tolerate the heat and the cells die. The surrounding healthy cells are not affected because the temperature is within a tolerable range. In addition, to the death of the unwanted cells, the immune system is provoked and promotes the healing of the treated area.

With respect to heat ablation therapies: these therapies, under development or in practice, are therapies that use thermal energy to preferentially heat diseased areas of tissue to a temperature sufficient to cause cell death. Thermal energy forms being utilized include microwave, radio frequency (RF) and high frequency ultrasound energy (HIFU). Both microwave and RF therapy systems are currently being marketed worldwide. Heat ablation techniques, if they are broadly applied, burn the tissue, causing irreversible damage to peripheral tissue due to protein denaturation, and destruction of nerves and blood vessels. Furthermore, heat generation causes secretion of substances from the tissue which may endanger the surrounding area. Thus, it is desirable to focus and minimize the application to heat.

"Brachytherapy", is a form of radiotherapy where a radiation source is placed inside or proximate to the area requiring treatment. Brachytherapy is commonly used to treat cancers of the cervix, bladder, prostate, breast, and skin. Brachytherapy can also be used in the treatment of (but not limited to) tumors of the brain, eye, head and neck region (lip, floor of mouth, tongue, nasopharynx and oropharynx), respiratory tract (trachea and bronchi), digestive tract (esophagus, gall bladder, bile-ducts, rectum, anus), urinary tract (bladder, urethra, penis), female reproductive tract (uterus, vagina, vulva), and soft tissues. Thus, the present invention provides devices manufactured using 3-dimensional printing to treat tumors and other diseases of these organs and regions of the body of a subject.

Brachytherapy can be used alone or in combination with other therapies such as surgery, External Beam Radiotherapy (EBRT) chemotherapy thermosurgery, cryosurgery and photodynamic therapy.

Exemplary sources of radiation of use in brachytherapy include, without limitation, $^{137}Cs$, $^{60}Co$, $^{192}Ir$, $^{125}I$, $^{103}Pd$ and $^{106}Ru$.

Brachytherapy contrasts with unsealed source radiotherapy in which a therapeutic radioisotope is injected into the body to chemically localize to the tissue which requires destruction. It also contrasts to EBRT, in which high-energy x-rays (or occasionally gamma-rays from a radioisotope, e.g., cobalt-60) are directed at the tumor from outside the body. Brachytherapy utilizes the precise placement of short-range ionizing radiation-sources (radioisotopes) directly at the locus of the disease, e.g., the tumor. In standard brachytherapy, the radiation source(s) is enclosed in a protective capsule or wire which allows the ionizing radiation to escape to treat and kill surrounding tissue, but prevents the charge of radioisotope from moving or dissolving in body fluids. The capsule may be removed later, or (with some radioisotopes) it may be allowed to remain in place permanently. In the present invention, the source of ionizing radiation is localized within the one or more curvature constrained channels withing the device of the invention. The device of the invention optimizes a key feature of brachytherapy; the irradiation only affects a localized area around the radiation sources. The present invention further limits the exposure of healthy tissue remote from the ionizing radiation source. Thus, exposure to radiation of healthy tissue further away from the source of ionizing radiation than the diseased tissue is reduced. In addition, using the device of the invention, if the patient moves or if there is any movement of the tumor within the body during treatment the source of ionizing radiation retains its correct position in relation to the tumor. These characteristics of brachytherapy provide advantages over EBRT—the tumor can be treated with very high doses of localized ionizing radiation, whilst reducing the probability of unnecessary damage to surrounding healthy tissues.

"Additive manufacturing" or "3-dimensional (3-D) printing" is a process of making a three-dimensional object of virtually any shape from a digital model. 3D printing uses an additive process in which successive layers of material are laid down in different shapes under computer control. 3D printing is considered distinct from traditional machining techniques, which remove material from a starting blank by methods such as cutting or drilling (i.e., subtractive processes).

The Embodiments

The Device

In an exemplary embodiment, the invention provides a removeably implantable device customized to contact an internal surface of a body cavity of a subject in which the device is implanted. An exemplary device is configured to provide localization of at least one local means of tumor control to a diseased tissue of the subject. The diseased tissue is within the body cavity and is contacted by the device or it is sufficiently proximate to the body cavity that the device delivers a therapeutically effective dose of the local means of tumor control to the diseased tissue. An exemplary device includes, (a) a device body with an exterior surface configured to contact at least a portion of the internal surface of a body cavity in which said device is installed or implanted. Within the exterior surface is an internal region having at least one curvature constrained channel disposed therein. The channel includes at least one opening communicating with the external surface. In various embodiments, the channel has two openings, each communicating with a different zone of the exterior surface of the device. An exemplary device of the invention also includes at least one local means of tumor control disposed within at least one curvature constrained channel. In an exemplary embodiment, the device is configured such that its outer surface is in contact with essentially all of the surface of the internal cavity of the subject in which it is implanted.

Figure 1:
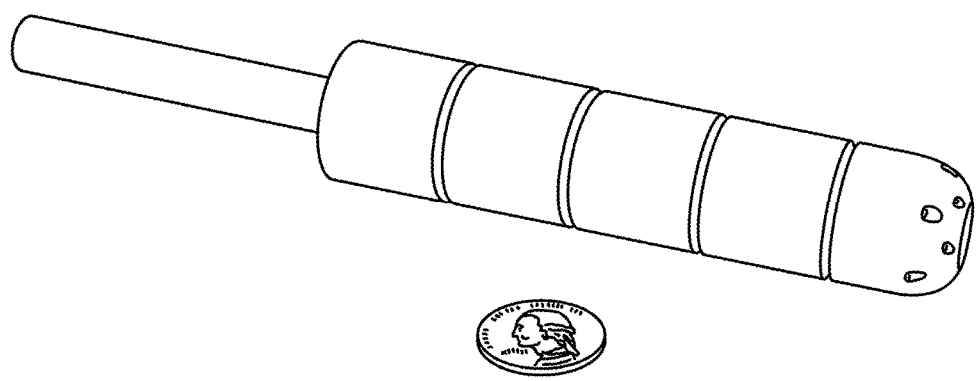
FIG. 1 is an intra-cavitary HDR GYN applicator: vaginal cylinder.
Figure 2:
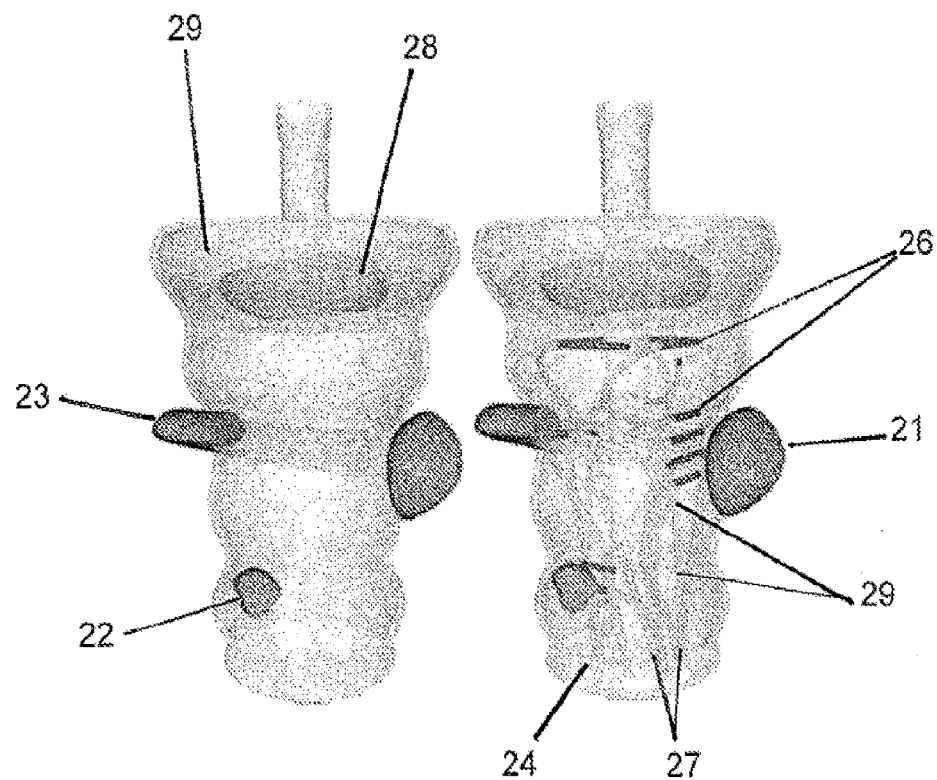
FIG. 2 is a GYN custom applicator with/out shielding.

FIG. 2 illustrates an exemplary device of the invention. The device has an exterior surface 29 and an internal region 24 into which curvature constrained channels 29 are disposed. The channels include an opening 27 communicating with the exterior surface of the device. Sources of ionizing radiation 26 are disposed within the channels proximate to regions of neoplastic tissue 21, 22, 23, and 28.

The local means of tumor control can be any means recognized in the art, particularly those of demonstrated therapeutic utility. In various embodiments, the local means of tumor control is selected from a chemotherapeutic agent, a source of cold, a source of ionizing radiation, a source of heat, a source of light, and a combination thereof. The local means of tumor control can be printed into or onto the device and it is optionally a permanent feature of the device. In an exemplary embodiment, the at least one local means of tumor control is removably insertable into at least one curvature constrained channel of the device. In this embodiment, the device is optionally configured such that the at least one local means of tumor control is removably insertable from outside the body of said subject after the device is implanted in the body cavity of the subject.

The present invention, in certain embodiments, provides the advantage of precisely positioning the local means of tumor control in register with the region of diseased tissue. Thus, in various embodiments, the at least one local means of tumor control is disposed within the device at a site selected such that, when the device is implanted in the body cavity of the patient, the at least one local means of tumor control is registered with the diseased tissue to be treated by the local means of tumor control. Devices according to this embodiment, are configured such that the at least one local means of tumor control is directed towards the diseased tissue and delivers a therapeutically effective dose of the at least one local means of tumor control sufficient to control at least a portion of the tumor.

Exemplary devices of the invention are configured such that a lower dose of the local means of tumor control is delivered to normal tissue proximate to the region of diseased tissue than current devices than would be delivered by currently known analogous treatment regime. Thus, according to the present invention, application of the device results in less ablation of the subject's normal tissue proximate to the region of diseased tissue than would be ablated by an identical therapeutically effective amount of said local means of tumor control administered in the absence of said device.

Figure 3A:
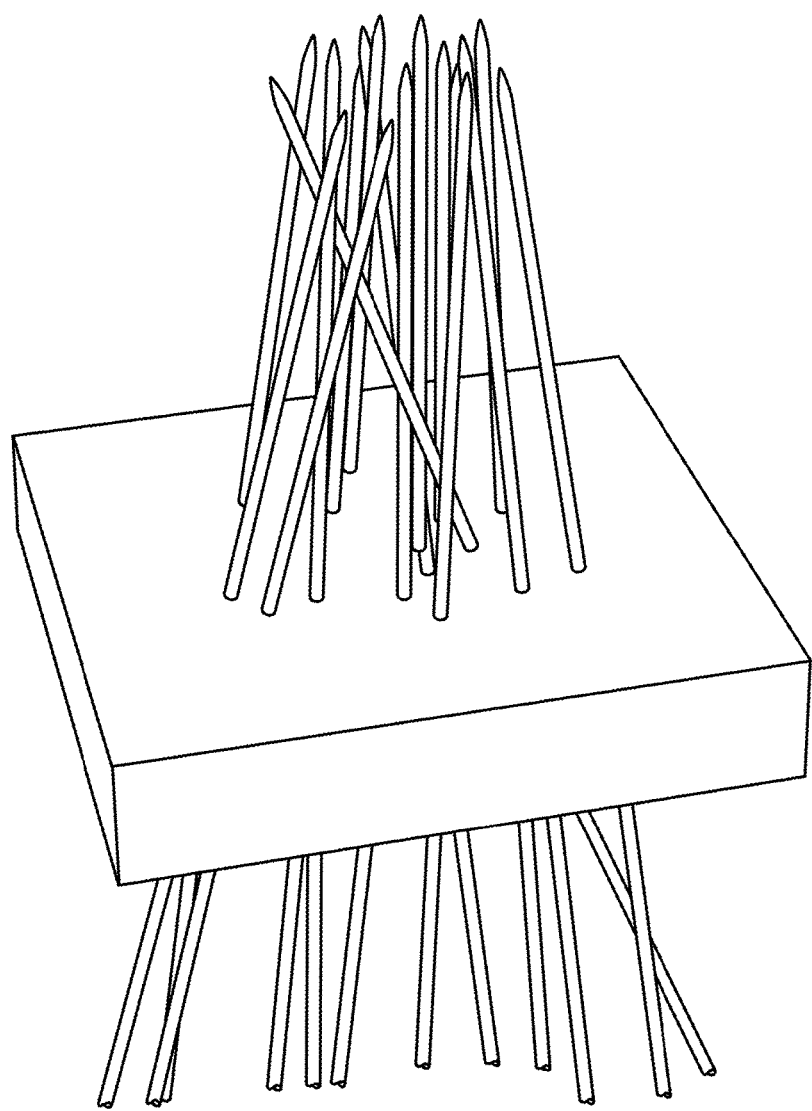
FIGS. 3A-C are HDR prostate templates for skew-line catheters.
Figure 3B:
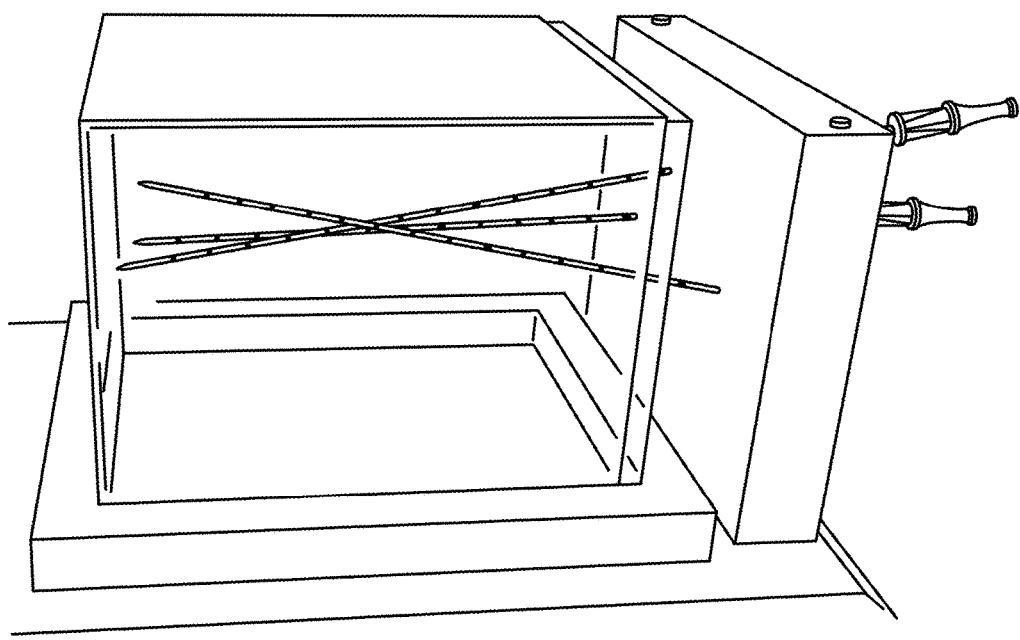
Figure 3C:
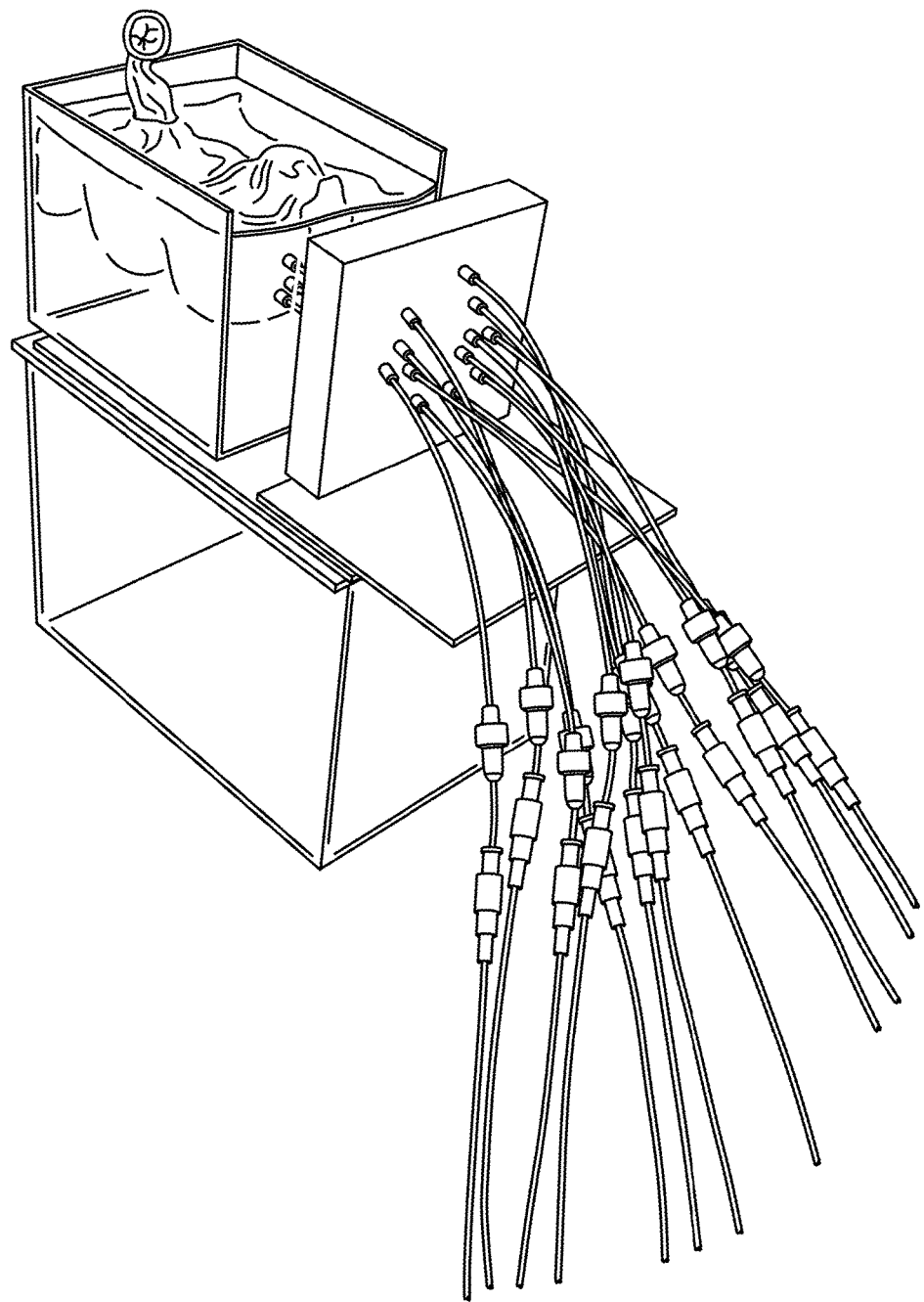
Figure 5:
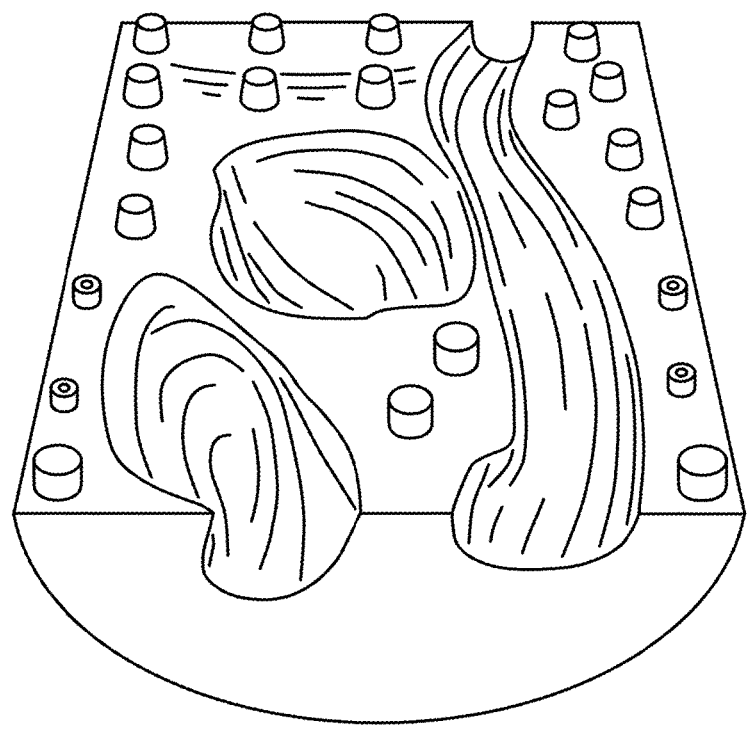
FIG. 5 is a phantom design for evaluation of deformable image registration tools.
Figure 6A:
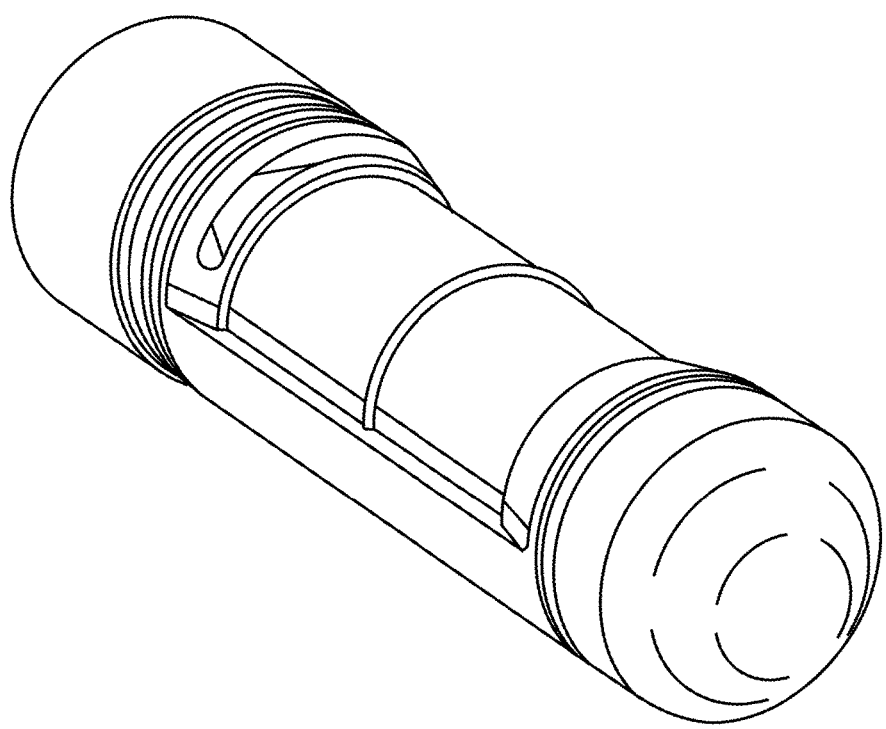
FIGS. 6A-C show the design and implementation of a device designed to combine hyperthermia and radiation therapy.
Figure 6B:
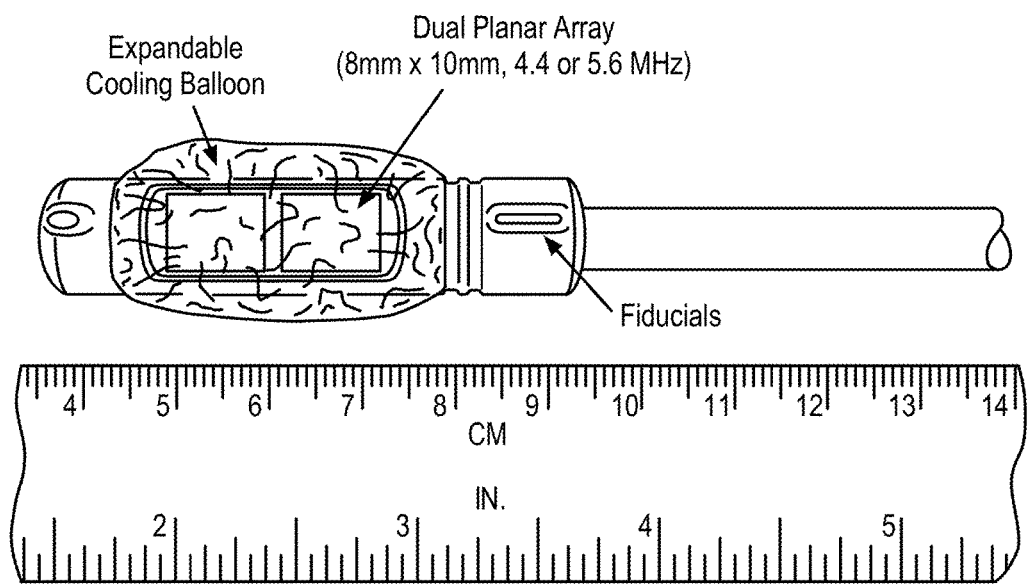
Figure 6C:
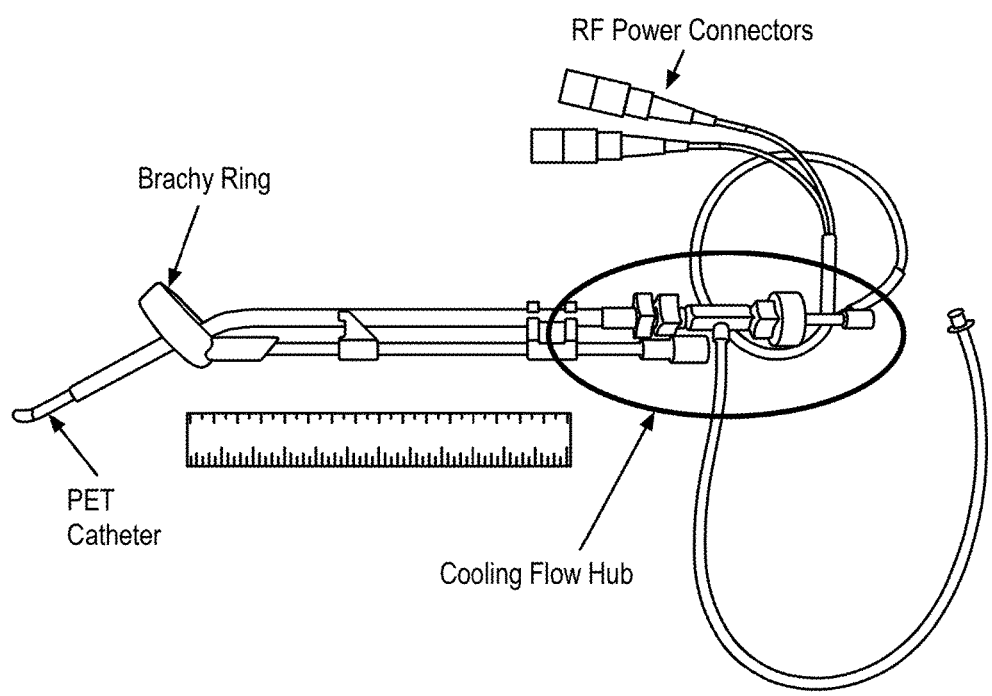

For example, the present invention provides a device and a method for directing ionizing radiation preferentially to the region of diseased tissue that provides delivery of less radiation to normal tissue proximate the diseased tissue than art-recognized devices such as those illustrated in FIG. 3, FIG. 4 and FIG. 10.

Figure 16:
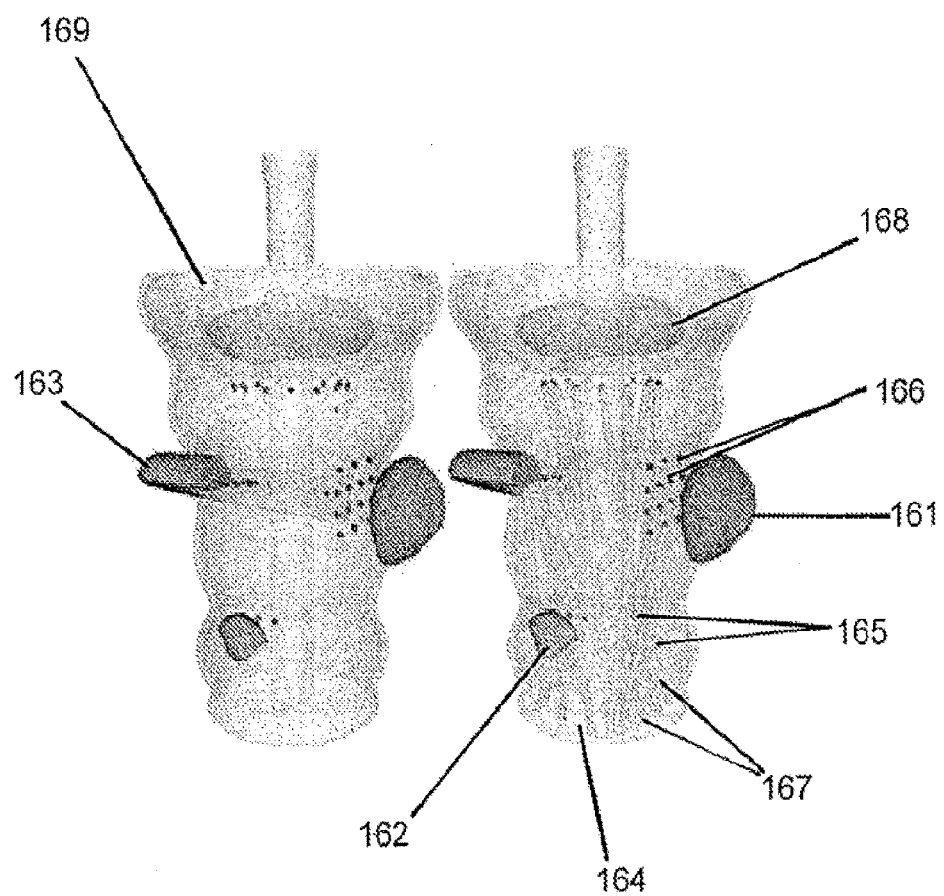
FIG. 16 provides views of a 3D printed implant with only linear channels: Left: 40 reachable dwell positions and segments. Right: achievable linear channels.

FIG. 16 shows a 3D printed device in which 169 in which the channels 165 in the internal region of the device 164 are linear channels with an opening 167 at the external surface of the device. The device provides dwell points 166 at multiple tumor sites 161, 162, 163 and 168.

Figure 15A:
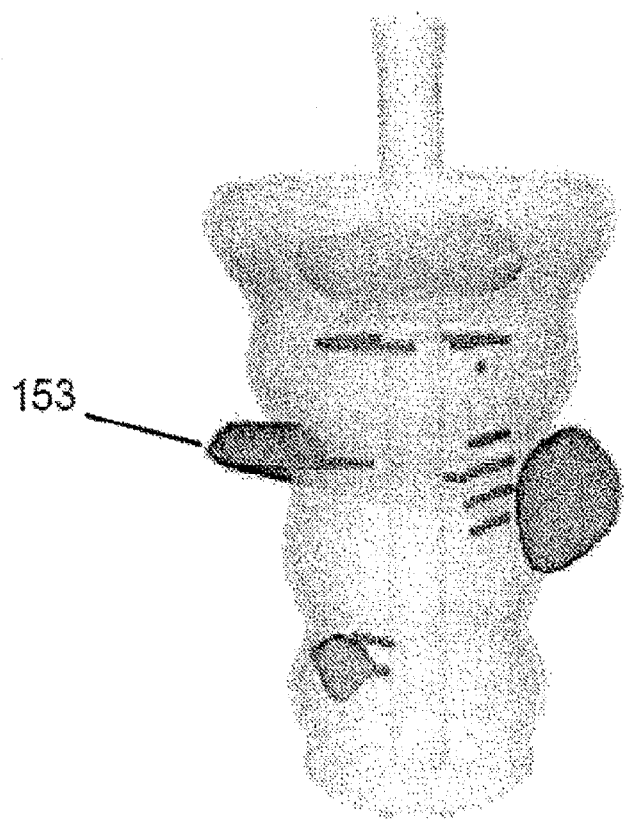
FIGS. 15A and 15B are 3D printed implant with curved channels by the CLA algorithm: Left: 149 reachable dwell positions and segments. Right: channels computed by the CLA algorithm.
Figure 15B:
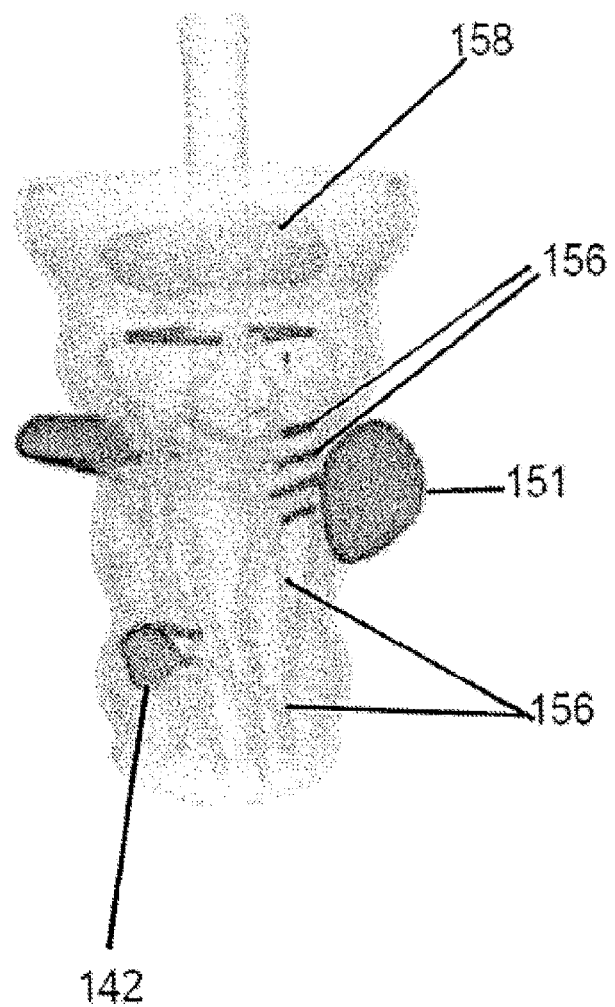

FIG. 15A and FIG. 15B display representative devices of the invention. FIG. 15B shows a printed implant with dwell points 156 located in curvature constrained channels 154, adjacent to tumors 142, 151, 153, and 158 (FIG. 15A).

In various embodiments, the device of the invention includes a region of shielding that blocks at least a portion of the tissue ablative effects of the tissue ablation means from reaching normal tissue proximate to the region of diseased tissue. In various embodiments, the shielding material is disposed at a position selected from the internal region, the at least one curvature constrained channel, the exterior surface, a region between the curvature constrained channel and the exterior surface, and a combination thereof. The shielding material can be the same material as that from which the bulk of the device is formed or it can be a different material. The shielding material can be a solid or a liquid. In various embodiments, the shielding material is a liquid within one or more curvature constrained channel or other channels or compartments of the device.

In various embodiments, the device of the invention is printed from more than one material or more than one class of material. For example, a device printed from one or more polymerizable organic monomers, organic polymers and metals is within the scope of the instant invention. In an exemplary embodiment, the device of the invention includes at least one region of a second material that at least partially blocks the tissue ablating effects of the local means of tumor control incorporated in the device. In an exemplary embodiment, this second material is a high Z material. This material preferably at least partially blocks the passage of particles emitted by a source of ionizing radiation. Thus, in one embodiment, there is provided a device in which at least one zone of the device body, or a curvature constrained channel comprises a shielding material capable of essentially blocking the tissue ablating effect from said at least one local means of tumor control disposed within said at least one curvature constrained channel.

Figure 18A:
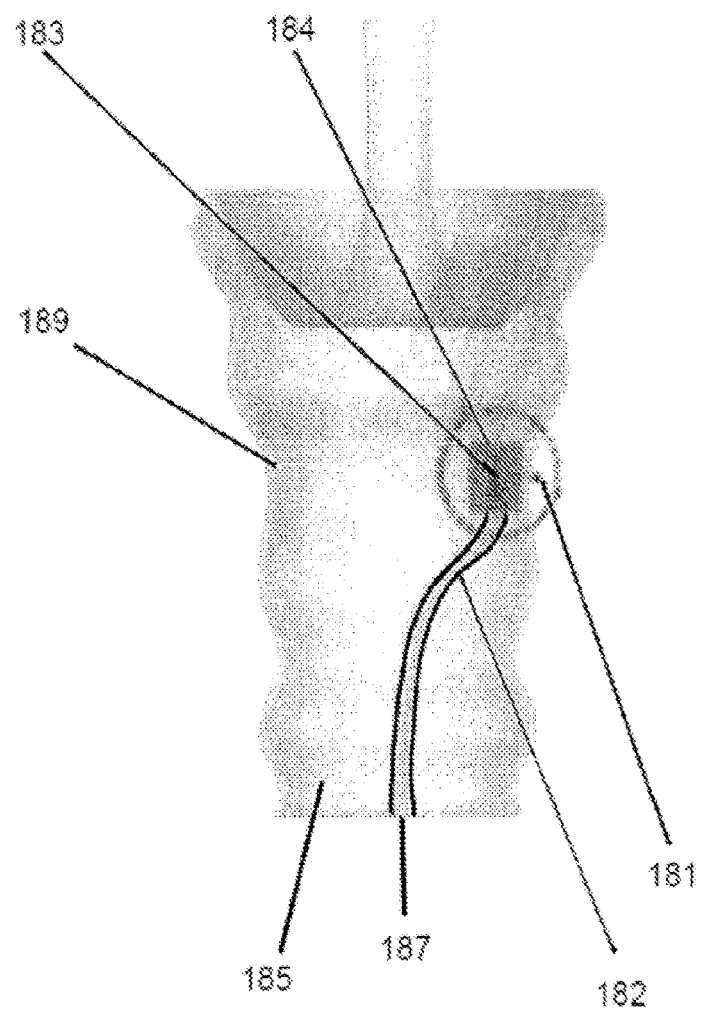
FIGS. 18A and 18B. Illustration of how lead shielding is incorporated into the implant as it is now possible to include multiple materials during 3D printing fabrication. (A) channel 182 proximal to a small tumor 181. (B) is a close-up view of the source 183, channel 182, and lead shielding 184, the latter with a small cylindrical void 184a that serves as a "targeting window" to allow radiation to be emitted toward the tumor 181 while shielding nearby health tissue.
Figure 18B:
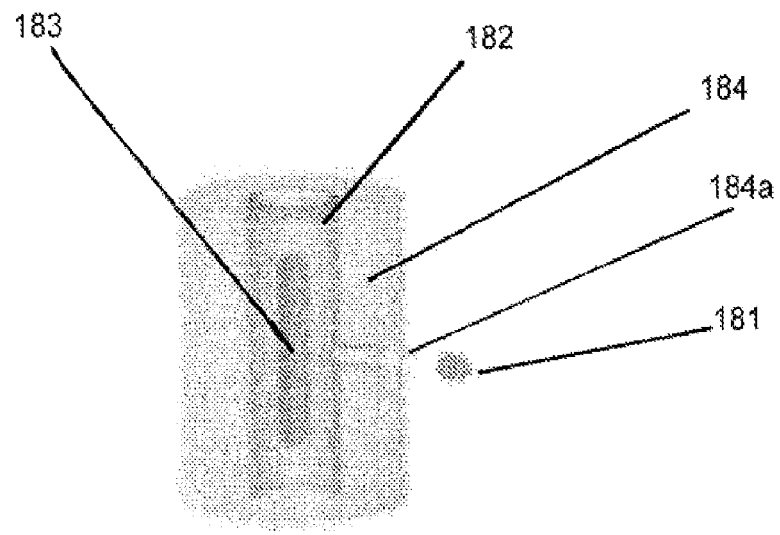
Figure 19:
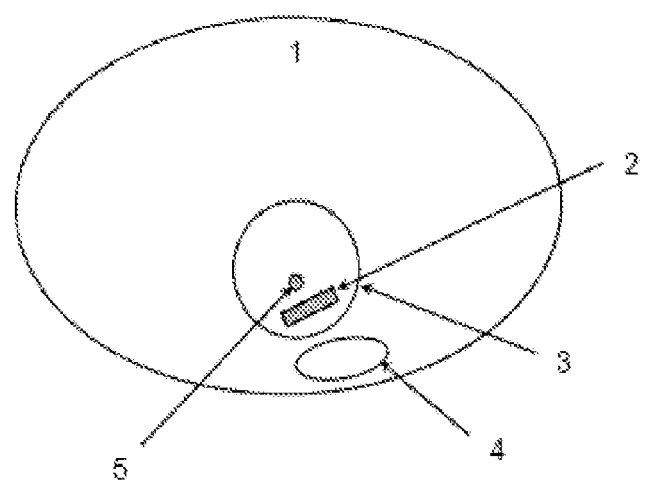
FIG. 19 is a view of an exemplary implanted device of the invention, showing device 3 implanted in patient 1. The device includes a sealed radiation source (5), with an area of shielding (2) between the source and an organ at risk (4). (1) patient; (2) radiation shield made of high-Z material; (3) applicator (also referred to as implant in document); (4) organ at risk (to be protected from radiation); and (5) sealed radioactive source.
Figure 20:
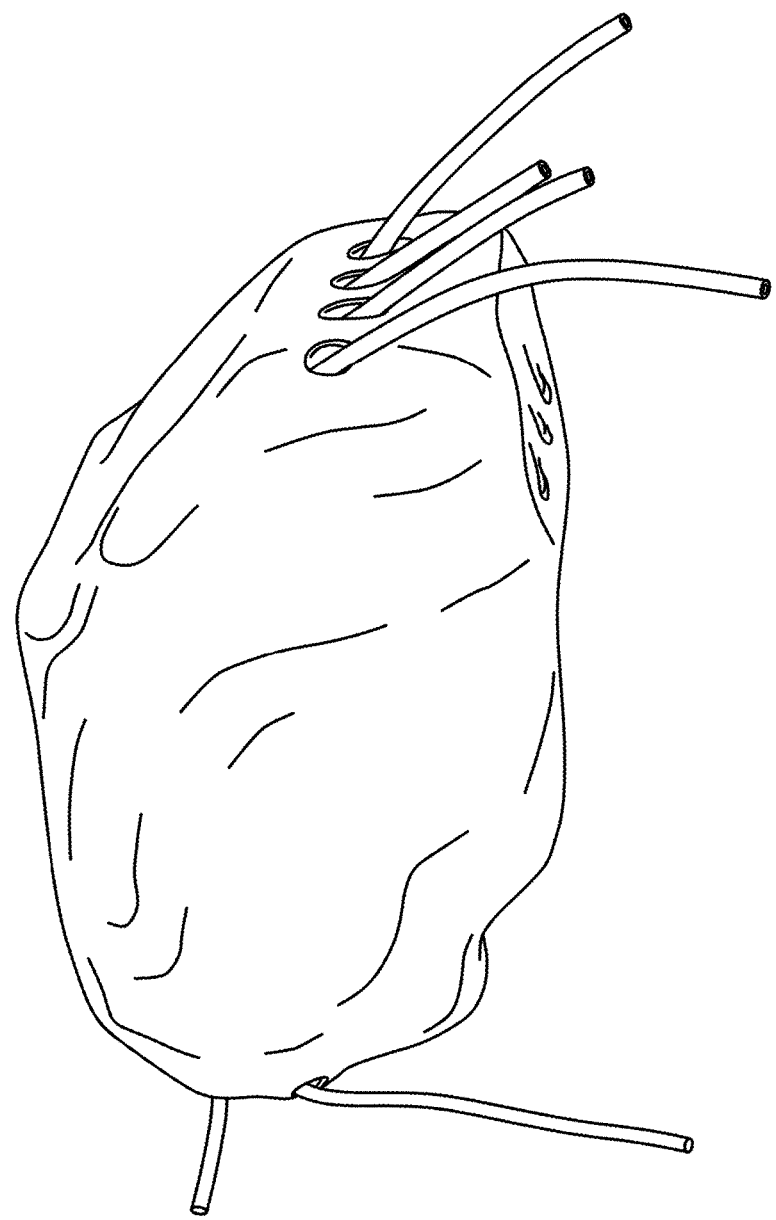
FIGS. 20 and 21 are images of an implant with wires threaded through the channels.
Figure 21:
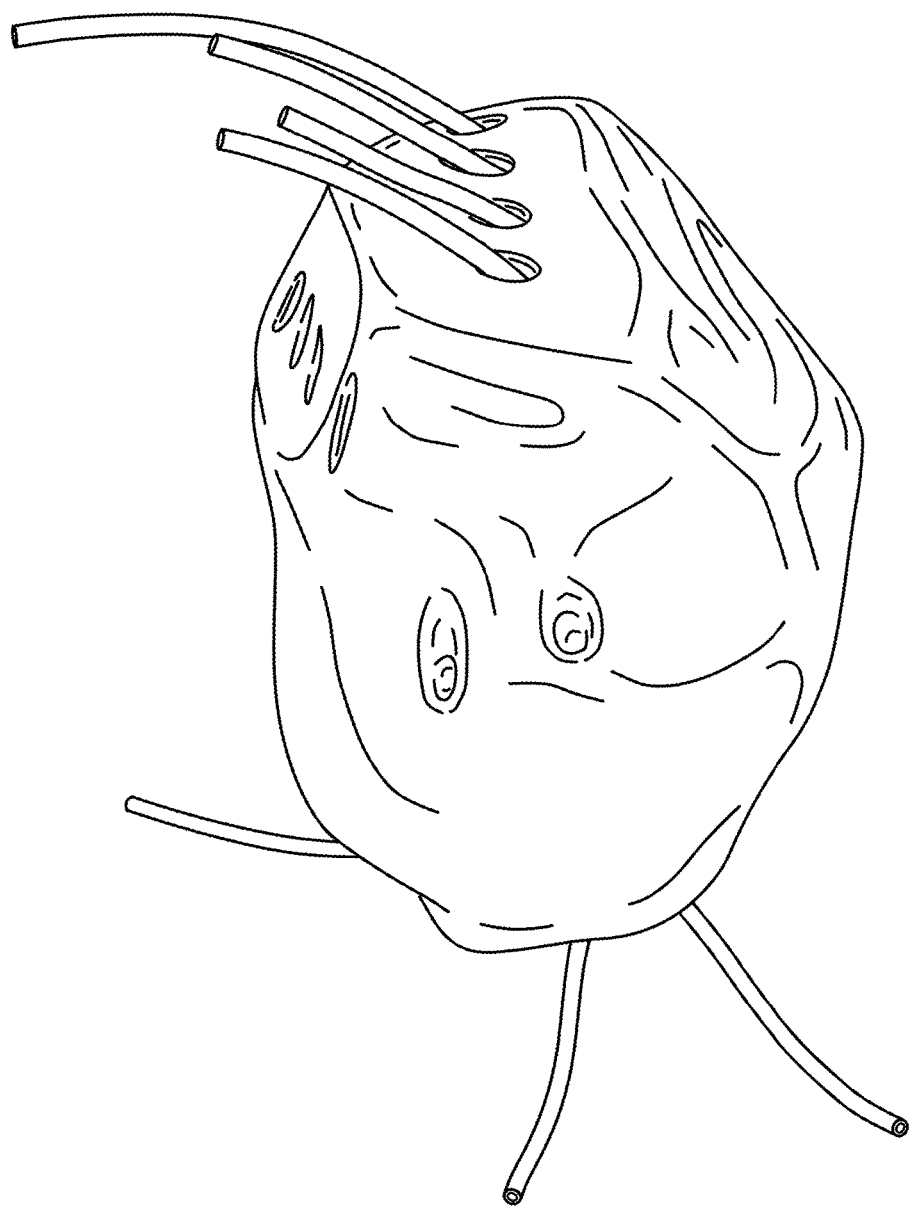
Figure 22:
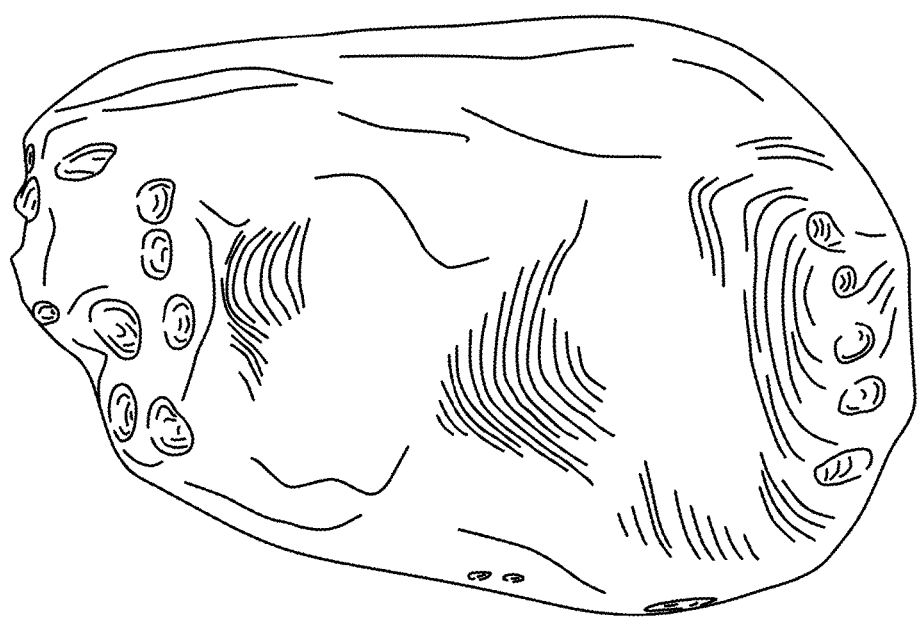
FIG. 22 is a view from the bottom of the implant.
Figure 23A:
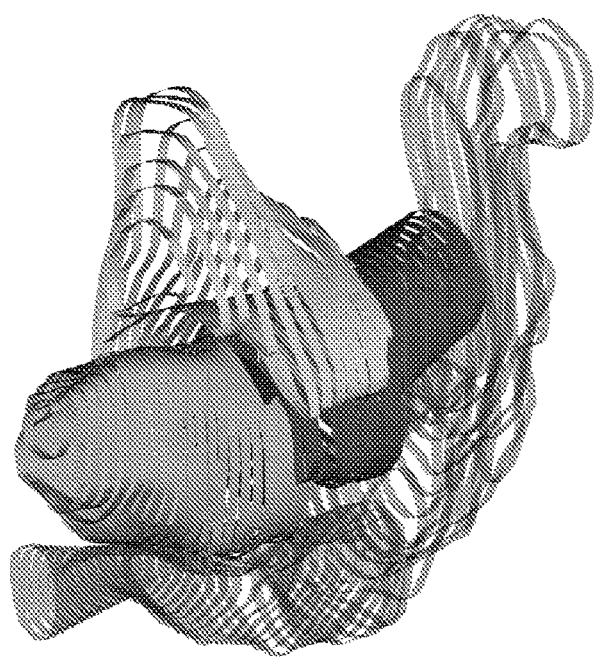
FIG. 23A is a ribbon model of a patent anatomy as viewed in Slicer3D.
Figure 23B:
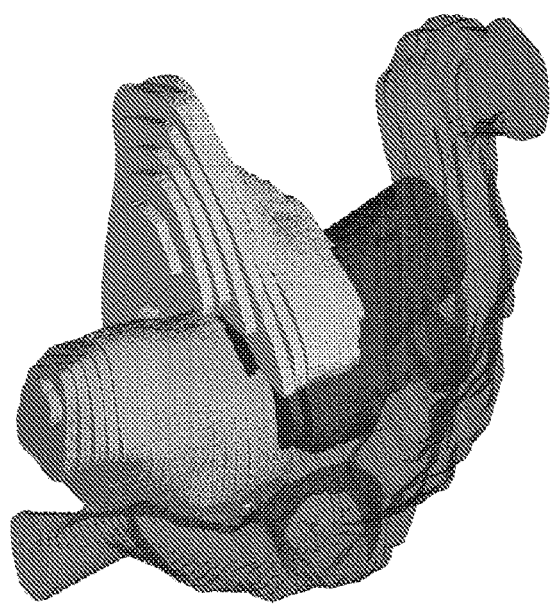
FIG. 23B is a closed volume model of a patient anatomy after reconstruction as viewed in Slicer3D.
Figure 24:
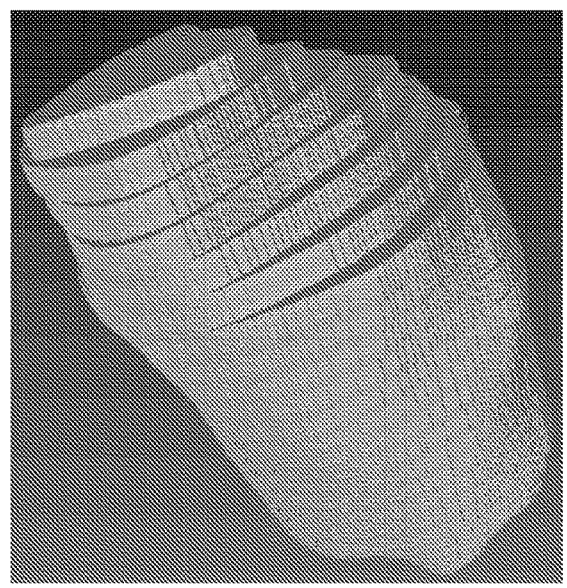
FIG. 24 is a view of an un-smoothed mesh (.stl) as output from Slider3D.
Figure 25A:
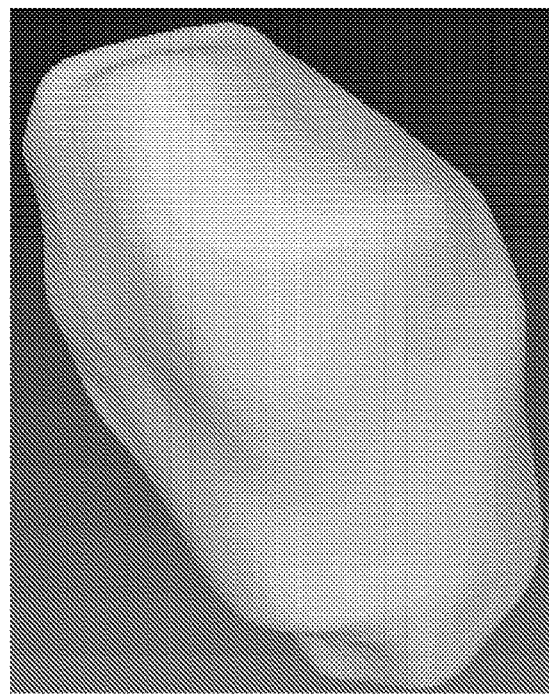
FIG. 25A is a view of a mesh file (.stl) for vaginal cavity.
Figure 25B:
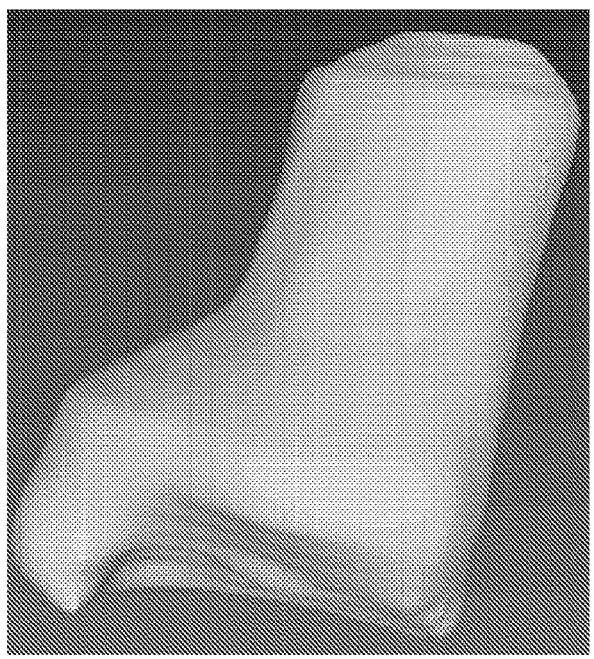
FIG. 25B is a view of a mesh file of a tumor after smoothing in Meshlab.
Figure 26:
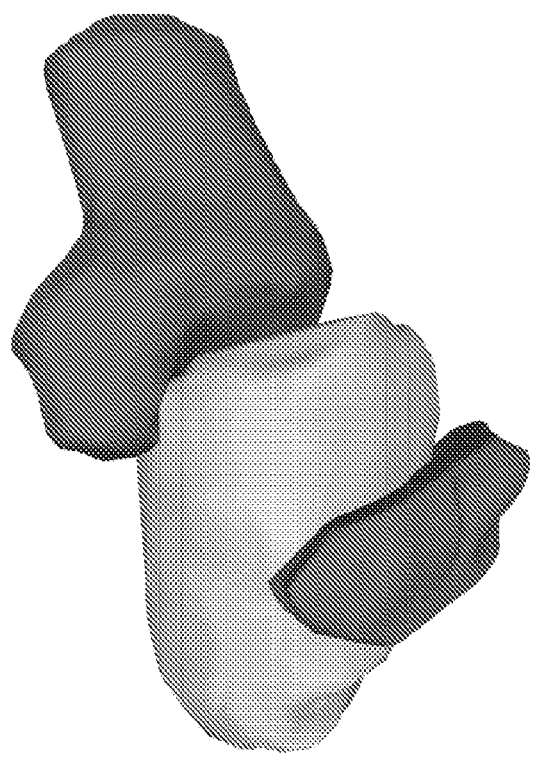
FIG. 26 is a view of a side tumor designed in CAD software. The tumors are shown as dark masses and the vaginal cavity is shown in light grey.
Figure 27:
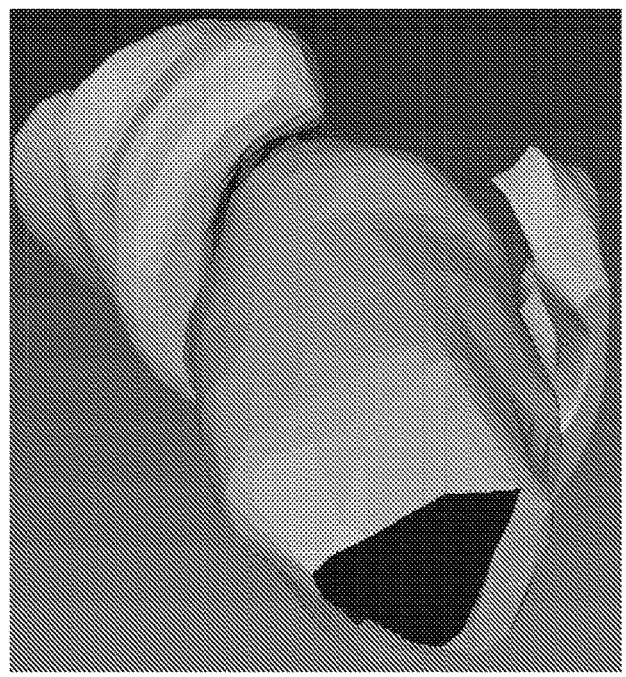
FIG. 27 is a view of a vaginal cavity opened up at the bottom. The dark region is the interior of the cavity.
Figure 28A:
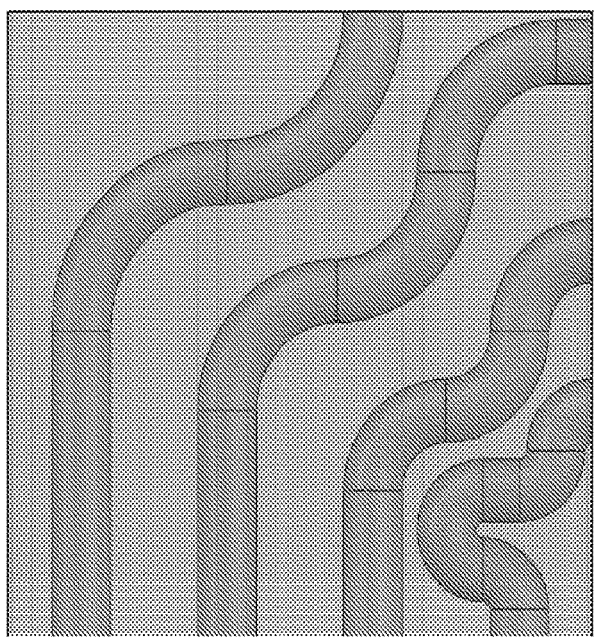
FIG. 28A is a top view of the test template for empirical evaluation of the channel parameters.
Figure 28B:
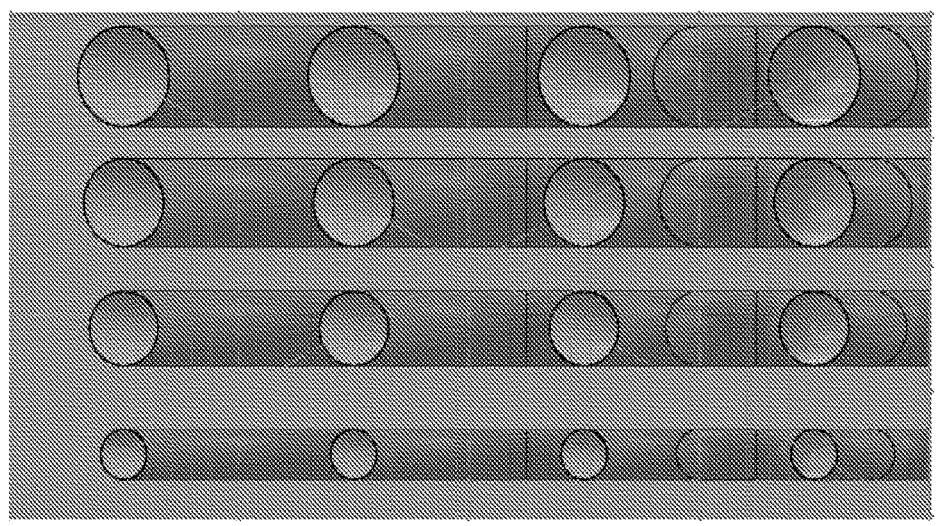
FIG. 28B is a side view of the test template for empirical evaluation of the channel parameters.
Figure 29:
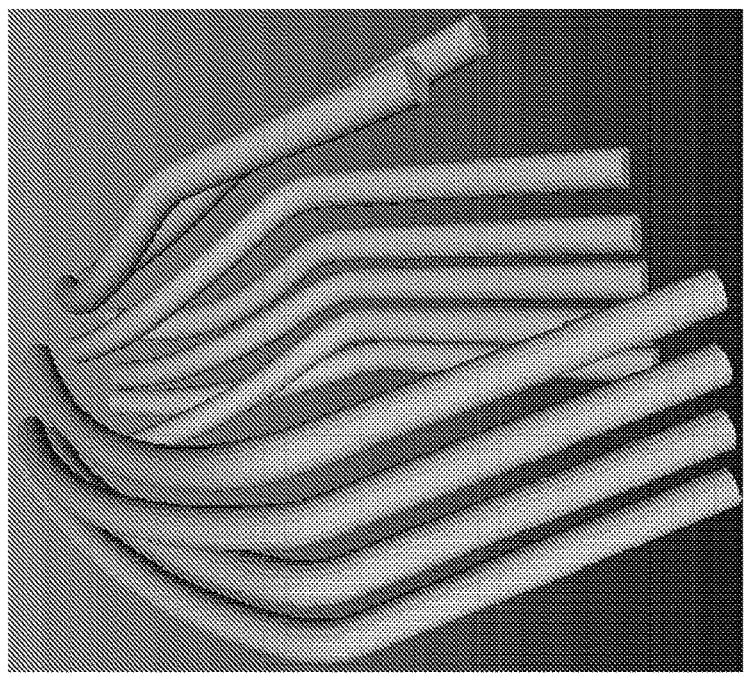
FIG. 29 is a view of the paths as output from the channel planning algorithm after being made into cylindrical channels using a CAD software and output as a .stl file.
Figure 30A:
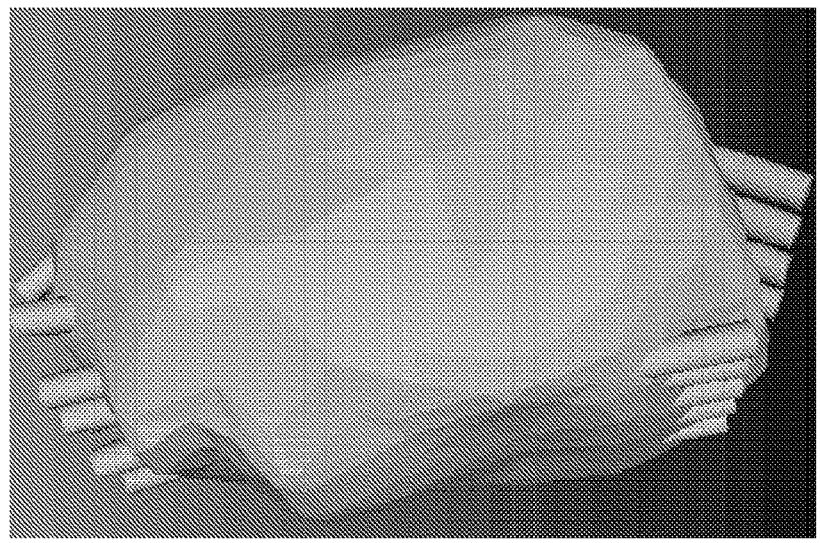
FIG. 30A is a mesh file for channels before the mesh difference operation seen in MeshLab.
Figure 30B:
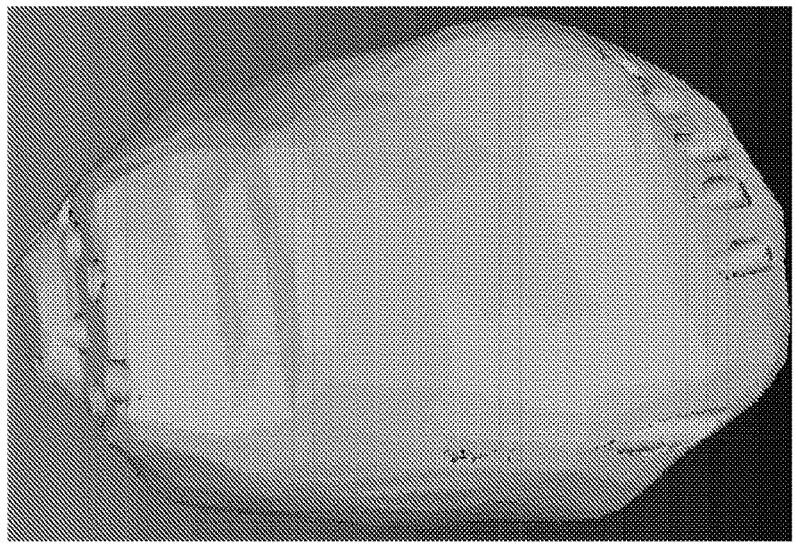
FIG. 30B is a mesh file for channels after the mesh difference operation seen in MeshLab.
Figure 31A:
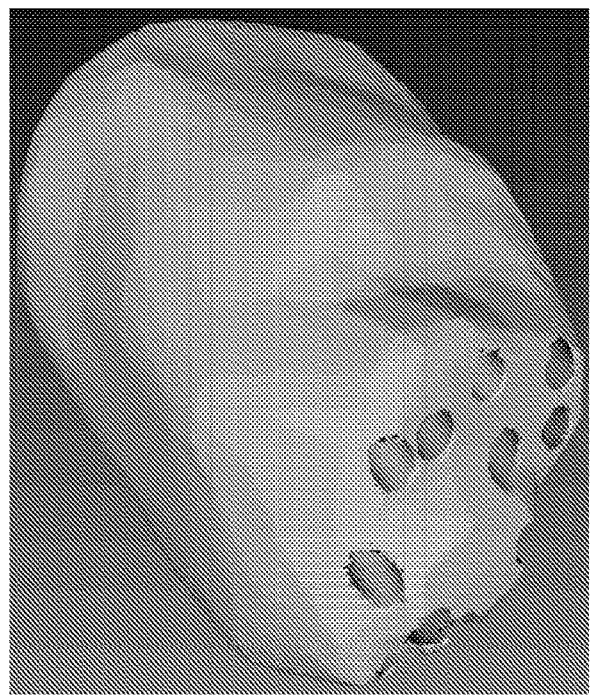
FIG. 31A is a view of the final mesh with hollow internal curved channels from a bottom view.
Figure 31B:
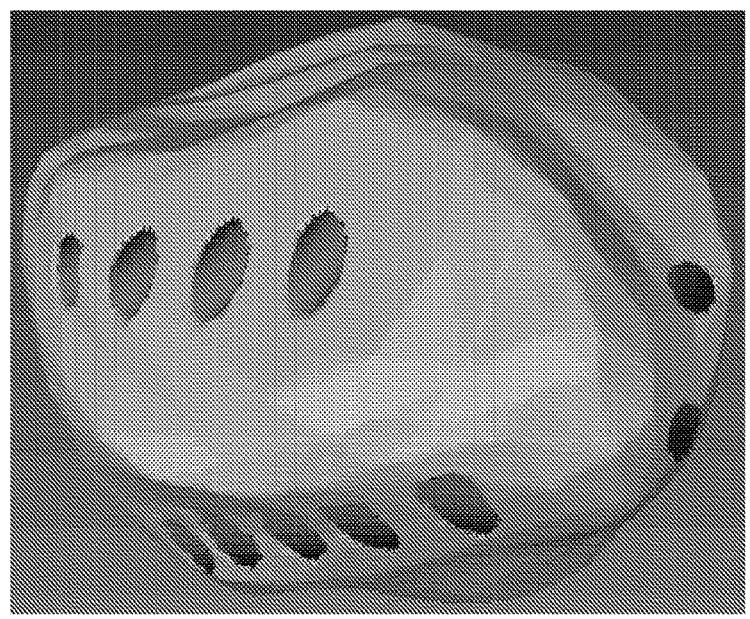
FIG. 31B is a view of the final mesh with hollow internal curved channels from a top view.
Figure 32:
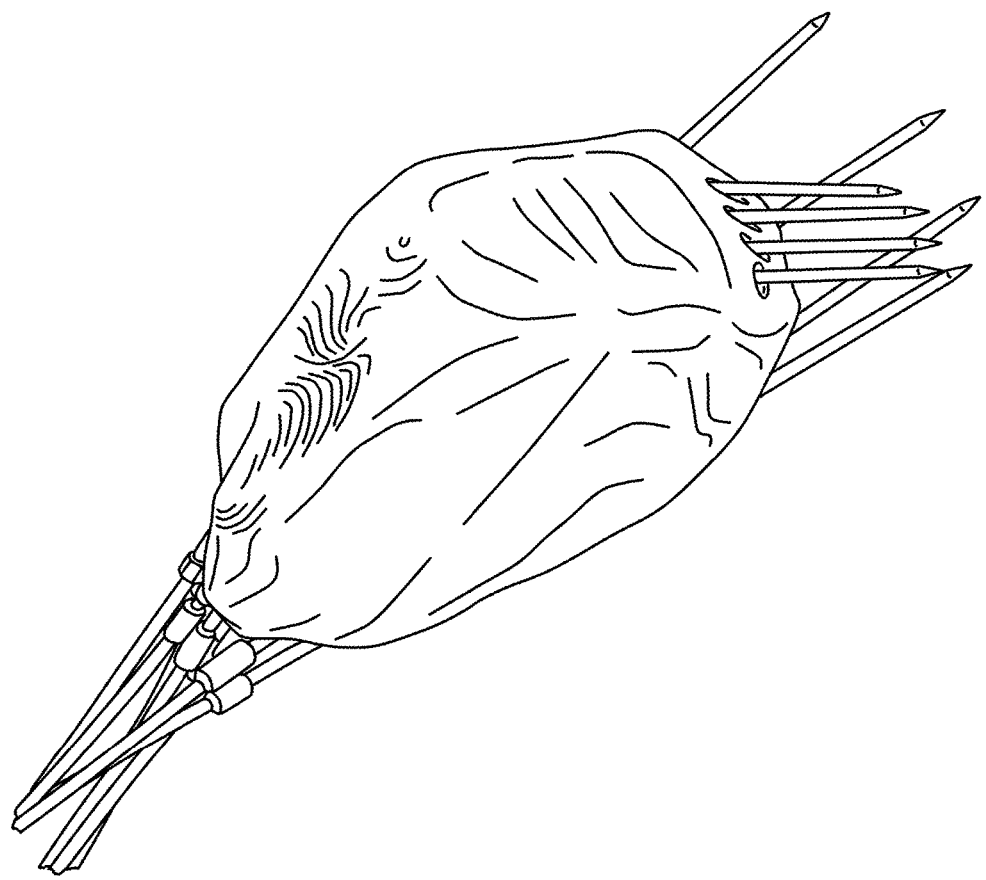
FIG. 32 is a view of an implant with catheters going through the channels. The rubber stoppers at the bottom of the catheter haven't been set to the correct length as mentioned in the text below.

FIG. 18 and FIG. 19 illustrate representative embodiments in which shielding is incorporated into the device. With respect to FIG. 18A, the device includes an external surface 189 and an internal region 185 in which curvature constrained channels 182, having an opening 187 to the external surface are disposed. A source of ionizing radiation 183 is located in a channel proximate to a region of neoplastic tissue 181. The source is shielded by radiation shield 184. FIG. 18B is an enlargement of a selected region of FIG. 18A showing the location of source 183 within channel 182. The source is shielded by radiation shield 184, which includes a targeting window lacking shielding 184a, which allows ionizing radiation to be directed towards tumor 181. FIG. 19 shows another exemplary embodiment in which 1 is a representation of the patient, 2 is a radiation shield made of high Z material 3 is the device of the invention, 5 is a source of ionizing radiation and 4 is an organ or other tissue to be protected from the ionizing radiation.

In various embodiments, the device is configured to provide the effects of the local means of tumor control to two or more loci within a single region of diseased tissue or within at least one locus within two or more regions of diseased tissue. In an exemplary embodiment, this goal is accomplished by a device provided with two or more curvature constrained channels. Thus, in an exemplary embodiment, the device of the invention includes at least two said curvature constrained channels. In an exemplary embodiment, none of the at least two curvature constrained channels intersect. In an exemplary embodiment, the device includes more curvature constrained channels than channels not curvature constrained.

It has been recognized that a device with only curvature constrained channels provides advantages in targeting the effects of the at least one local means of tumor control. Thus, in an exemplary embodiment, the invention provides a device having no channels that are linear channels, e.g., FIG. 15B vs. FIG. 16.

Recent advances in 3D printing (also known as additive manufacturing) are poised to have major impact on many fields as described by Lipson (H. Lipson and M. Kurman, *Fabricated: The New World of 3D Printing*. Wiley, 2013) and Gershenfeld (N. Gershenfeld, "Fab: The coming revolution on your desktop—from personal computers to personal fabrication," 2007) Jacobs (P. F. Jacobs and D. T. Reid, *Rapid prototyping & manufacturing: Fundamentals of stereolithography*. Society of Manufacturing Engineers in cooperation with the Computer and Automated Systems Association of SME, 1992) is an early introduction. Non-toxic, FDA approved materials are allowing 3D printed parts to be used for medical applications (F. P. W. Melchels, J. Feijen, and D. W. Grijpma, "A review on stereolithography and its applications in biomedical engineering," *Biomaterials*, 31:6121-30, August 2010) such as bone replacement (H. Seitz, W. Rieder, S. Irsen, B. Leukers, and C. Tille, "Three-dimensional printing of porous ceramic scaffolds for bone tissue engineering," *Journal of biomedical materials research. Part B, Applied biomaterials*, 74:782-8, August 2005) and oral surgery implants (J. D'haese, T. Van De Velde, A. Komiyama, M. Hultin, and H. De Bruyn, "Accuracy and complications using computer-designed stereolithographic surgical guides for oral rehabilitation by means of dental implants: a review of the literature," *Clinical implant dentistry and related research*, 14:321-35, June 2012).

Thus, in an exemplary embodiment, the device of the invention is manufactured by 3D printing of a material capable of being 3-D printed. Exemplary materials capable of being 3D printed include metals, polymerizable monomers and polymers, both organic and inorganic. In an exemplary embodiment, the material is an organic polymer. FIGS. 20-24 are views of an exemplary device of the invention manufactured by 3D printing.

Other than printability, the material is selected to have any desirable property, for example, in various embodiments, the material is selected from a material that is permeable to light of a frequency appropriate for phototherapy, conducts heat, allows the passage of ionizing radiation and a combination thereof.

In an exemplary embodiment, the material from which the device is manufactured is sterilizable. In various embodiments, the material and resulting device is sterilizable by STERRAD (Advanced Sterilization Products, Irvine, Calif.). In various embodiments, the material has dose attenuation properties at $^{192}$Ir energies essentially similar to water. In various embodiments, the material has sufficiently equivalent dose attenuation properties to water at $^{192}$Ir energies to be compatible with the brachytherapy planning system and workflow. An exemplary material also does not produce CT artifacts. In an exemplary embodiment, the material is PC-ISO (Stratasys, Eden Praririe, Mn).

Figure 7:
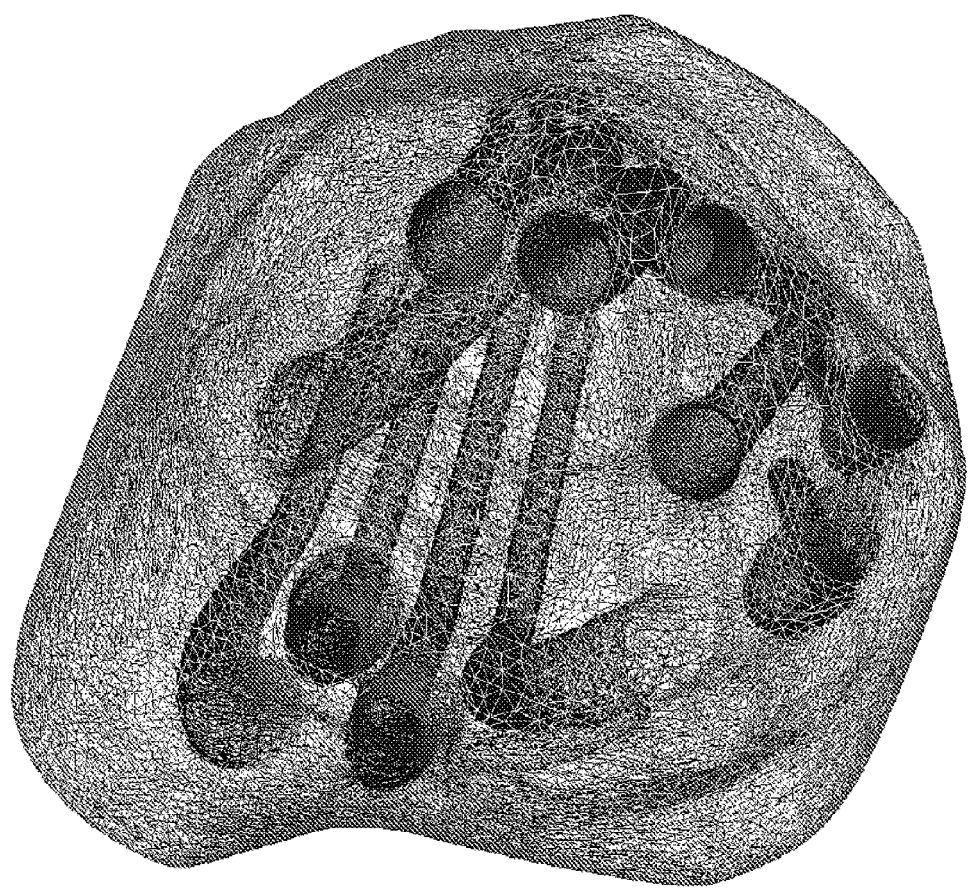
FIG. 7 is a bottom view of a device of the invention.
Figure 8:
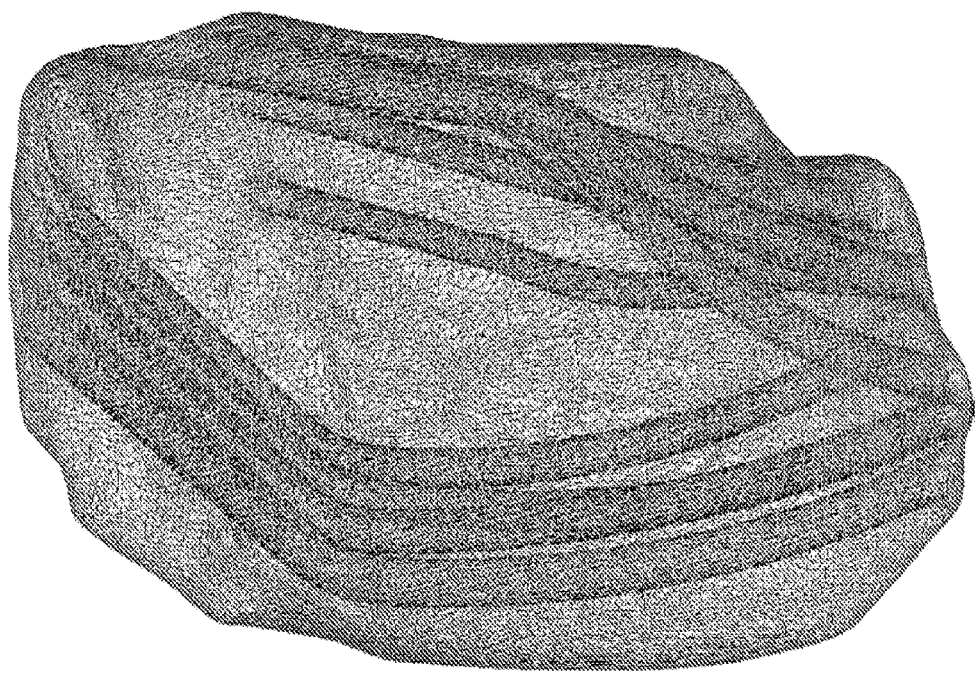
FIG. 8 is a side view of the device of FIG. 7.
Figure 9:
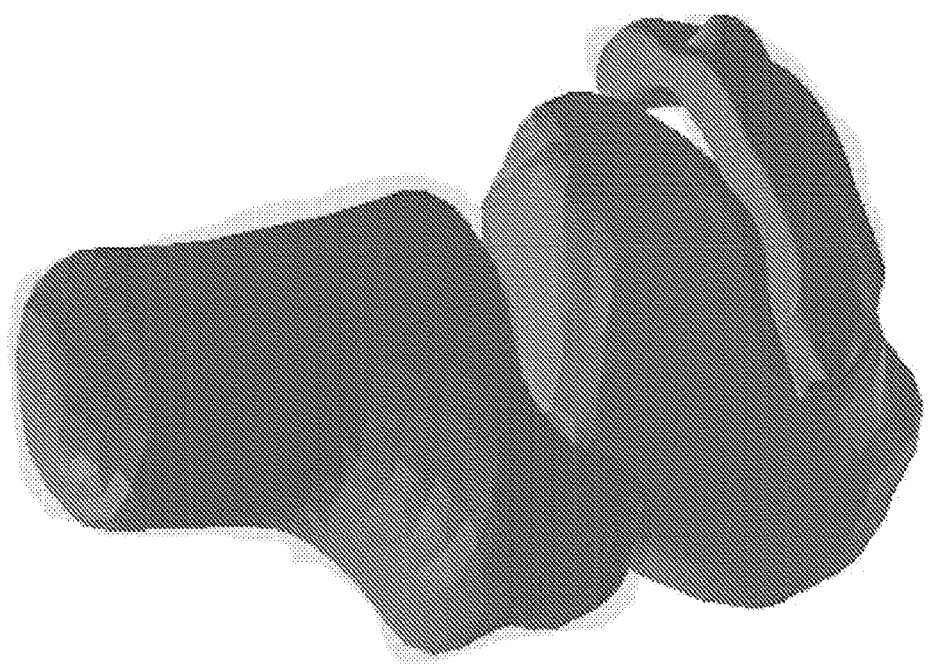
FIG. 9 is a view of a model of the anatomy of a subject from which the device of FIG. 7 is designed and printed.

An advantage of the present invention is the ability to register the delivery of the effects of the tissue ablation means with the region of diseased tissue. Moreover, the device of the invention can be designed with reference to data acquired from the subject through one or more diagnostic imaging modality (FIG. 9). One or more of the designs of the device, proper placement of the device and calculation of the dosage of the tissue ablation means delivered to both diseased and normal tissues by the device is readily correlatable with diagnostic images acquired from the subject. Moreover, the width, length arc and position of the at least one curvature constrained channel can be determined using such imaging data (FIG. 7, FIG. 8). These images can be taken either or both before and after installation of the device. The invention provides a device allowing the ready registration tissue ablation means with the region of diseased tissue using one or more imagable fiducial marker incorporated into the device. In an exemplary embodiment, the device and its incorporated fiducial marker are configured for registration between at least one region of anatomy of the subject and at least one diagnostic image of the region of anatomy. In an exemplary embodiment, the one or more region of anatomy is selected from a region of diseased tissue and a region of normal tissue proximate to the area of normal tissue.

As will be appreciated by those of skill in the art, the imaging modality of use in the present invention is any modality capable of providing useful data regarding the fiducial marker and the region of anatomy of the subject. Exemplary modalities include, without limitation, MRI, CT, gamma camera scintigraphy, PET, ultrasonography and a combination thereof. Thus, the invention provides a device in which the fiducial marker is imageable by MRI, CT, gamma camera scintigraphy, PET, ultrasonography or a combination thereof.

In an exemplary embodiment, the device of the invention is substantially solid with the exception of the curvature constrained channels, and other channels or compartments that contain various materials, e.g., shielding materials. The invention, however also encompasses light weight devices that are substantially hollow in which the curvature constrained channels and other channels and compartments are luminal structures disposed within a device body that, with the exception of these channels and compartments, is substantially hollow.

The at least one local means of tumor control is located at any useful point or region within the device. In an exemplary embodiment, the at least one local means of tumor control is disposed at a position within at least one curvature constrained channel, forming at least one dwell point. Various devices of the invention include two or more dwell points in registration with one or more regions of diseased tissue within said patient upon implantation of the customized device of the invention (FIG. 2, 15B). The device optionally includes one or more shielding regions adjacent to a dwell point. The device further optionally includes one or more fiducial markers providing an imageable means for determining the position of the means of tissue ablation.

In various embodiments, the device of the invention is not intended for implantion but rather to be overlaid on a region of a subject's body for the treatment of tumors on or below the skin. In various embodiments, the curved channels discussed in the context of the impantable device are also a component of the overlaid device. In various embodiments, the curved channels are designed such that they place a local means of tumor control sufficiently proximal to a tumor to ablate the diseased tissue and, in a preferred embodiment, provide therapeutic advantage. The other design and structural elements discussed in the context of the implantable device, e.g., local means of tumor control source, shielding and the like can be components of the overlaid device. As will be apparent to one of skill in the art, in some embodiments, it may be efficacious for the device to have a combination of implantable and overlaid regions and it can be readily designed and printed to have any desirable combination of such regions.

The Methods

In addition to the devices disclosed herein, the invention provides a method of treating a region of diseased tissue using one or more devices of the invention. For example, the invention provides a method of treating a disease in a patient by implanting a device of the invention in a body cavity of the subject such that a therapeutically effective dose of a local means of tumor control contained within the device is delivered to a locus of the disease from at least one dwell point in the device. In an exemplary embodiment, the disease is a neoplastic disease. In various embodiments, local means of tumor control is a source of ionizing radiation.

As discussed hereinabove, an advantage inherent in the devices of the invention is the ability to precisely register the delivery of the effects of the local means of tumor control to a locus of diseased tissue. In an exemplary embodiment, a therapeutically effective dose of the local means of tumor control is delivered to the locus of disease from the dwell point.

As discussed hereinabove, exemplary devices of the invention include at least one fiducial marker. In an exemplary method of the invention, the at least one fiducial marker is utilized to align the dwell point with the locus of disease. The alignment is readily confirmed after implantation of the device by acquiring one or more images of the subject post-implantation.

The invention also provides methods of making a device of the invention. An exemplary method includes printing the device using additive manufacture, also referred to as 3-dimensional printing. In various embodiments, a 3-dimensional model of the body cavity is produced and the device is 3-dimensionally printed from the model.

Imaging technologies such as US, CT, and MRI are utilized to scan patient anatomy and localize cancers and then additive manufacturing technologies such as 3D printing are used to fabricate precise implants with external geometry matching the internal geometry of the patient cavity, with precise and not-necessarily-linear internal channels for the seeds to be moved through, and in a preferred embodiment to create or print additional channels for radioactive shielding such as lead that can shape the radiation field along desired directions along the paths.

In an exemplary embodiment, the method includes following steps:
   (a) creating a cast of the body cavity of the subject;
   (b) scanning the cast in three dimensions;
   (c) printing a planning device using 3-D printing directed by coordinates acquired from the scanning, the printing optionally including printing an imagable fiducial marker.

In another exemplary embodiment, the method includes the following steps:
   (a) Obtaining US, CT, or MR images of the tumor site and adjacent anatomy;
   (b) Digitally outlining the volume into which the applicator will be inserted; and
   (c) Printing a planning device using 3-D printing directed by coordinates acquired from the imaging, the printing optionally including printing an imagable fiducial marker.

In another exemplary embodiment, the method includes the following steps:
   (a) Measuring the cavity into which the applicator will be placed via digital exam by the physician;
   (b) Generating a digital model based on measurements; and
   (c) Printing a planning device using 3-D printing directed by coordinates acquired from the imaging, the printing optionally including printing an imagable fiducial marker.

Once the planning device is printed, whether the design is accurate and appropriate can be confirmed by the steps of:
   (a) Implanting the planning device in the body cavity of the subject;
   (b) Imaging the body cavity of the subject with the planning device implanted in said body cavity;
   (c) Computing dose and distribution of the local means of tumor control; and
   (d) Printing the therapeutic device using 3-D printing.

As will be apparent to those of skill in the art, in various embodiments, data from the imaging study is utilized to assemble a 3-dimensional model of anatomy specific to the subject corresponding to the imagable fiducial markers of said device.
wherein step (f) further comprises applying a channel layout algorithm with inverse dose planning to compute said at least one curvature constrained channel.

Algorithms of use in calculating the parameters of the one or more curvature constained channels are generally known in the art and examplary algorithms of use are discussed in the Examples that follow. Representative parameters calculated by such algorithms include the position, width, length and arc of the curvature constrained channel. The algorithm can also be used to calculate the position of one or more dwell location in a curvature constrained channel. In various embodiments, the method of planning and manufacturing the device further includes step (f), which comprises applying a channel layout algorithm with inverse dose planning to compute at least one of the dwell points for the means of tissue ablation (e.g., source of ionizing radiation) (FIGS. 7-8 and FIGS. 12-13).

3D printing technologies allow printing of a wide variety of materials including plastics, resins, and composites FDA-approved for human implant. Multiple materials can be printed in sequence, allowing complex devices to be printed. Metals such as aluminum, silver, and lead can also be printed. Thus, in an exemplary embodiment, the method includes printing the device of more than one material. In various embodiments, the method utilizes 3D printing to incorporate shielding (e.g., lead) into the implant as it is fabricated. This provides the ability to shield healthy tissue and direct radiation to small tumor targets as illustrated in FIGS. 18A and 18B. In various embodiments, one or more fiducial marker is printed on or into the device using 3D printing. In various embodiments, 3D printing is utilized to print one or more means of tissue ablation on or into the device. In an exemplary embodiment, the local means of tumor control is printed at a predetermined dwell point.

Figure 17A:
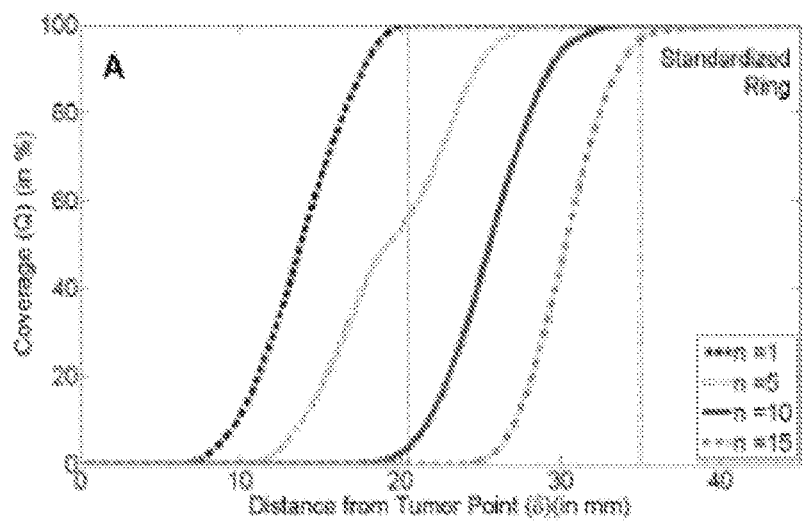
FIGS. 17A, 17B and 17C. Coverage metric for each of three treatment options: standardized ring implant (current practice), customized 3D printed implant with linear channels, and customized 3D printed implant with curved channels. Plot of quality 2 (percentage of tumor volume covered) at radiation radius of δ for 1, 5, 10, and 15 dwell positions respectively. (A) standardized ring implant. (B) 3D Printed implant with linear channels, and (C) 3D Printed implant with curved channels. The dashed vertical lines in each plot indicate the value of δ at which 2=100% is achieved for n=1 and n=10, respectively. Full tumor coverage is achieved with significantly lower radii in case (C).
Figure 17B:
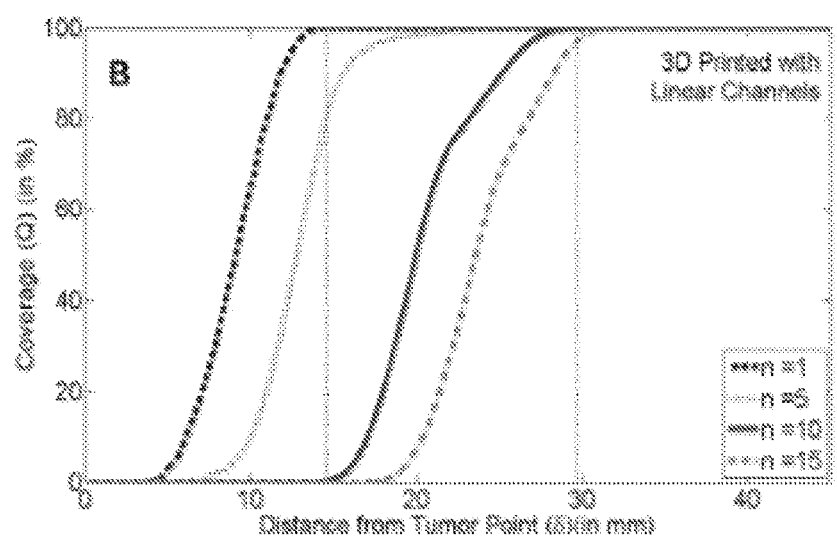
Figure 17C:
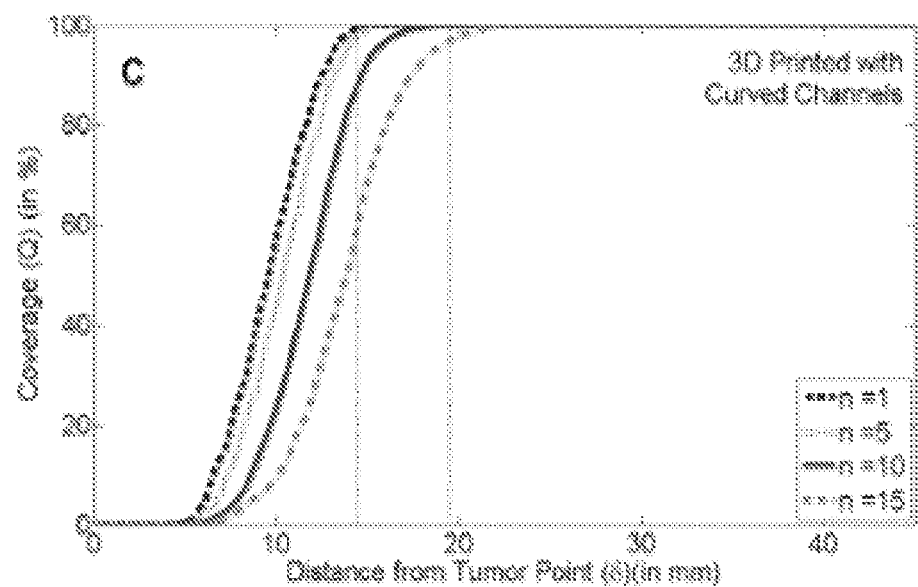

Exemplary embodiments of the device designed by the application of different algorithms for channel architecture are shown in FIG. 15, and the dosage results achieved with such devices are presented in FIG. 17B and FIG. 17C. For purpose of comparison, the dosage results with a conventional ring device are presented in FIG. 17A.

As will be apparent to those of skill in the art, in embodiments of the invention in which the device is designed to be overlaid on a selected surface of a subject's body (e.g., for treatment of tumors of the skin or tumors beneath the skin), the elements of such a device, its planning and printing are similar to those described above in the context of the implantable device. Useful variations of the process will be readily apparent and accessible to those or ordinary skill in the art without recourse to undue experimentation.

The following examples are offered to illustrate selected embodiments of the invention and are not limiting of the scope of the invention.

EXAMPLES

Example 1

Automation science has been applied to a number of healthcare applications to improve quality of treatment by improving repeatability and reliability. Huang et al. (Y. Y. Huang and K. H. Low, "Comprehensive planning of robotic therapy and assessment of task-oriented functions via improved {QFD} applicable to hand rehabilitation," in *Automation Science and Engineering (CASE), 2010 IEEE Conference on*, pp. 252-257, IEEE, 2010) studied planning of robotic therapy and assessment of task-oriented functions for hand rehabilitation. Tervo et al. (K. Tervo, L. Palmroth, and H. Koivo, "Skill Evaluation of Human Operators in Partly Automated Mobile Working Machines," *IEEE Transactions on Automation Science and Engineering,* 7:133-142, January 2010) and Solis et al. (J. Solis and A. Takanishi, "Towards enhancing the understanding of human motor learning," in 2009 *IEEE International Conference on Automation Science and Engineering*, pp. 591-596, IEEE, August 2009) explored the use of automation for studying human motor skills for medical task training. Mendez et al. (J. A. Mendez, S. Torres, J. A. Reboso, and H. Reboso, "Model-based controller for anesthesia automation," in 2009 *IEEE International Conference on Automation Science and*

Engineering, pp. 379-384, IEEE, August 2009) studied automatic control of anesthesia, and Subburaj et al. (K. Subburaj, B. Ravi, and M. G. Agarwal, "Automated 3D geometric reasoning in Computer Assisted joint reconstructive surgery," in 2009 *IEEE International Conference on Automation Science and Engineering*, pp. 367-372, IEEE, August 2009) studied computer assisted joint reconstruction surgery.

Garg et al. (A. Garg, T. Siauw, D. Berenson, A. Cunha, I.-C. Hsu, J. Pouliot, D. Stoianovici, and K. Goldberg, "Initial experiments toward automated robotic implantation of skew-line needle arrangements for {HDR} brachytherapy," in *Automation Science and Engineering (CASE), 2012 IEEE International Conference on*, pp. 26-33, 2012), addressed limitations imposed by standardized external templates for guiding linear needles for treatment of prostate cancer. It was demonstrated how a set of linear brachytherapy needles could be accurately delivered in a nonparallel (skew-line) pattern by a specialized robot to avoid puncturing sensitive organs. The present invention extends these ideas in several ways, providing a method of designing and 3D printing an implant with a geometry that precisely aligns with patient anatomy without the need to use a robot. The present invention also provides an algorithm for computing curved interior channels through the 3D printed implant for delivering radioactive sources and other tissue ablative therapies.

Pötter et al. (R. Pötter and C. Kirisits, "Upcoming ICRU/GEC ESTRO recommendations for brachytherapy in cancer of the Cervix (1)," *Radiotherapy and Oncology*, 103:S42, 2012; R. Pötter, C. Haie-Meder, E. V. Limbergen, I. Barillot, M. D. Brabandere, J. Dimopoulos, I. Dumas, B. Erickson, S. Lang, A. Nulens, and Others, "Recommendations from gynaecological (GYN) GEC ESTRO working group (II): Concepts and terms in 3D image-based treatment planning in cervix cancer brachytherap 3D dose volume parameters and," *Radiotherapy and oncology*, 78(1):67-77, 2006) present recommendations on intracavity BT dose distributions for gynecological cancers. There are a number of commercially-available implants/applicators for treating cervical and endometrial cancers: Fletcher applicators (L. Delclos, G. H. Fletcher, E. Bailey Moore, and V. A. Sampiere, "Minicolpostats, dome cylinders, other additions and improvements of the Fletcher-Suit afterloadable system: Indications and limitations of their use," *International Journal of Radiation Oncology Biology Physics*, 6(9):1195-1206, 1980), Utretch applicator (M. Bernstein, K. J. Mehta, R. Yaparpalvi, H. Kuo, and S. Kalnicki, "Results of the Hybrid Interstitial-Intracavitary Utrecht Applicator for cervical cancer in an Outpatient setting," *Radiotherapy and Oncology*, 103:S116, 2012) Vienna applicator (J. C. A. Dimopoulos, C. Kirisits, P. Petric, P. Georg, S. Lang, D. Berger, and R. Pötter, "The Vienna applicator for combined intracavitary and interstitial brachytherapy of cervical cancer: Clinical feasibility and preliminary results," *International Journal of Radiation Oncology Biology Physics*, 66(1):83-90, 2006) and Mold type applicators (N. Magné, C. Chargari, N. SanFilippo, T. Messai, A. Gerbaulet, and C. Haie-Meder, "Technical aspects and perspectives of the vaginal mold applicator for brachytherapy of gynecologic malignancies," *Brachytherapy*, 9(3):274-277, 2010). These standardized implants can be combined with linear catheters as illustrated in FIG. 10. Used by many radiation oncologists, these intracavitary applicators include an intrauterine tandem and intravaginal ovoids, producing a pear-shaped dose distribution centered on the cervix, allowing a high dose to be delivered to the cervix while sparing bladder and rectum. Although these systems allow some adaptation to patient anatomy, patient movement (and filling of bladder and bowels) can cause shifts in the applicator position that result in undesired doses.

One exciting innovation is the approach described by Magne et al. (N. Magné, C. Chargari, N. SanFilippo, T. Messai, A. Gerbaulet, and C. Haie-Meder, "Technical aspects and perspectives of the vaginal mold applicator for brachytherapy of gynecologic malignancies," *Brachytherapy*, 9(3):274-277, 2010), which proposes use of a customized implant created with a plaster vaginal impression that accurately shows the topography and extension of tumors and the specific anatomy of the vagina and cervix. In their experiments, two linear catheters and tandem shaft are inserted by the oncologist into the implant. The authors report decreased relative movement of implant while the patient is mobile over three days, thereby enabling less error between planned and delivered dose distributions. Treatment of patients with tumor extensions to the endometrial tissue of the vaginal wall often requires two separate implants if treated with standard applicators. A custom implant allows the oncologist to account for tumor extensions in a single iteration. The authors report their experience with more than 5000 patients and note that their method has three main advantages: personalized, tailored treatment, MRI procedure compatibility without image quality disturbance, and increased patient comfort. We note that Magne et al prepare the mold implant manually and correct placement of catheters is highly dependent on oncologist's experience.

The present example illustrates a device and method in which a plaster cast is scanned (or the patient anatomy segmented from MRI or CT scans) to create a precise 3D model that is provided as input to an algorithm for computing a set of internal curved channels that can be embedded into a 3-D printed implant of the invention.

External templates for guiding linear needles for brachytherapy have also been studied. Roy et al. (J. N. Roy, K. E. Wallner, L. L. Anderson, and C. Ling, "CT-based optimized planning for transperineal prostate implant with customized template," *International Journal of Radiation Oncology Biology Physics*, 21:483-489, July 1991) explored the use of precision machining of linear needle paths. These templates and paths were not generated algorithmically.

A growing body of research has been reported on motion planning for steering needles (V. Duindam, R. Alterovitz, and K. Goldberg, "Motion planning for steerable needles in 3D environments with obstacles using rapidly-exploring Random Trees and backchaining," in 2008 *IEEE International Conference on Automation Science and Engineering*, pp. 41-46, IEEE, August 2008; S. Patil and R. Alterovitz, "Interactive Motion Planning for Steerable Needles in 3D Environments with Obstacles," *Proceedings of the . . . IEEE/RAS-EMBS International Conference on Biomedical Robotics and Biomechatronics. IEEE/RAS-EMBS International Conference on Biomedical Robotics and Biomechatronics*, pp. 893-899, January 2010; N. J. Cowan, K. Goldberg, G. S. Chirikjian, G. Fichtinger, R. Alterovitz, K. B. Reed, V. Kallem, W. Park, S. Misra, and A. M. Okamura, "Robotic needle steering: Design, modeling, planning, and image guidance," in *Surgical Robotics: System Applications and Visions* (J. Rosen, B. Hannaford, and R. M. Satava, eds.), ch. 23, pp. 557-582, Springer, 2011). The objective is to steer a flexible needle with curvature constraints through tissue to internal targets by exploiting asymmetries at the needle tip. Such needles can reach targets that cannot be reached by stiff linear needles. The needle is a nonholonomic system and is related to motion planning for fixed-wing aircraft (M. Hwangbo, J. Kuffner, and T. Kanade, "Efficient Two-phase 3D Motion Planning for Small Fixed-wing UAVs," in *Proceedings 2007 IEEE International Conference on Robotics and Automation*, pp. 1035-1041, IEEE, April 2007; J. Le Ny, E. Feron, and E. Frazzoli, "On the Dubins Traveling Salesman Problem," *IEEE Transactions on Automatic Control*, 57:265-270, January 2012).

Computing a set of internal channels is a similar problem in that curvature is constrained but has the distinct advantage that there is no uncertainty due to tissue properties or needle mechanics: channels can be printed with extreme accuracy. It is also important that channels do not intersect. We build on prior work by Patil et al. (S. Patil and R. Alterovitz, "Interactive Motion Planning for Steerable Needles in 3D Environments with Obstacles," *Proceedings of the . . . IEEE/RAS-EMBS International Conference on Biomedical Robotics and Biomechatronics. IEEE/RAS-EMBS International Conference on Biomedical Robotics and Biomechatronics*, pp. 893-899, January 2010) which uses rapidly exploring random trees (RRT) (S. M. LaValle, *Planning Algorithms*. Cambridge, U.K.: Cambridge University Press, 2006. Available at http://planning.cs.uiuc.edu) for planning curvature constrained paths for steerable needles (N. J. Cowan, K. Goldberg, G. S. Chirikjian, G. Fichtinger, R. Alterovitz, K. B. Reed, V. Kallem, W. Park, S. Misra, and A. M. Okamura, "Robotic needle steering: Design, modeling, planning, and image guidance," in *Surgical Robotics: System Applications and Visions* (J. Rosen, B. Hannaford, and R. M. Satava, eds.), ch. 23, pp. 557-582, Springer, 2011).

An objective of the present example was to compute a set of non-intersecting curvature-constrained channels within the implant that reach targets proximal to tumors for delivery of radiation and if needed, a report of which tumor zones could not be reached.

The input is the registered pre-operative geometry from a combination of 3D scan of the plaster cast and CT (or MRI) scan of the patient (FIG. 9). This input includes: external geometry of the implant specified as a triangle mesh (FIGS. 7-8); the desired entry zone at the base of the implant for all channels; and the locations of tumors and organs-at-risk (OAR) (vaginal wall, cervix, rectum, urethra, bladder, uterus). The channel layout problem can then be stated as follows: given a 3D model of the implant volume I, which may include internal voids that will be treated as obstacles for channels, a set of 3D cancerous tumors that require radiation treatment, a specification of the entry region at the base of the implant E the maximum allowable entry angle (deviation from normal) $\alpha$, the minimum radius of curvature of the channel, $r_{min}$, and the channel diameter w, corresponding to the width of the catheter carrying the source, the objective is to compute a set of non-intersecting curvature constrained channels $C=\{C_1, C_2, \ldots, C_N\}$ starting from E that lie within I and are proximal to as much of the set T as possible.

The ability to deliver radiation doses depends on the arrangement of potential source dwell points and their proximity to tumors. The radiation dosage at radius r follows an inverse square law. The quality of an implant is measured by the percentage of tumor volume that is "covered" by the set of dwell points, where coverage is a function of coverage distance between a dwell point (source) and a tumor point (target). Higher quality reduces the maximum dwell time needed to treat tumors and in turn the potential for a hot spot that can harm healthy tissue. Alternate quality metrics can be based on inverse dose planning (J. Borg and D. Rogers, "Monte carlo calculations of photon spectra in air from $^{192}$Ir sources," *National Research Council Report PIRS-629r*, Ontario, Canada, 1999), which we will stud in future work.

To compare implants and channels for a given set of tumors T, the set of reachable dwell position and how thoroughly they "cover" the set of tumors was considered. Consider a set of reachable dwell positions S (for instance in case of 3D printed implants these are evenly spaced inside reachable dwell segments). The set of tumors was discretized into a set of evenly spaced points dT. The proximity of dwell position dS from a tumor point dT with the "coverage radius" $\delta$ was quantified such that: if dS lies within a ball of radius centered at dT, then dS is said to cover dT. It is also helpful to consider cases where tumor points can be covered by some multiple n of dwell points. Hence the cover C of dT is the set:

$$C(dT,\delta)=\{dS:\|dS-dT\|_2 \leq \delta_1 dS \in S\} \quad (1)$$

We defined the quality of coverage $Q(n, \delta)$ as the percentage of tumor volume such that each tumor point within that volume $dT \in T'$, $T' \subseteq T$ was covered by at least n dwell positions within a ball of radius $\delta$ centered at dT.

$$Q(n, \delta) = \frac{1}{|\mathcal{T}|} \int_{\mathcal{T}} I\{|C(dT, \delta)| \geq n\} dT. \quad (2)$$

where $I\{\bullet\}$ is the indicator function and $|\bullet|$ is set cardinality. Reaching 100% coverage with smaller radiation radius and more dwell positions can reduce occurrence of hot spots an increase dose conformality to the tumor geometry to spar healthy tissue.

The Channel Layout Algorithm (CLA) is summarized in Alg. 1. The first step was generating a set of dwell segment proximal to the given set of tumors. Starting from the dwell segment most distal to the entry zone, the curvature constraints were used to construct an RRT backward from the segment toward the entry zone, stopping if/when a channel was found that avoids obstacles. This channel was treated as an obstacle and considered the next dwell segment until all dwell segments were considered. Each step is described in detail below.

A. Generate Dwell Segments:

A candidate set of dwell segments was computed, which are linear segments near tumors that may include multiple potential source dwell positions. Curved dwell segments and segments in alternate orientations were also optionally considered.

Given the set of tumors T and the implant volume I, the set of dwell segments D was computed as follows. The implant volume was discretized with a regular voxel grid, where each voxel is a cube of side length equal to the channel width w. Since the surface of the implant volume was represented as a discretized triangular mesh, all the triangles were marked from which the outward facing surface normals intersect the tumor surfaces (FIG. 7, FIG. 8). Given the marked triangles, they were projected in the direction of the inward facing surface normal by a distance w to account for the channel width, and all voxels intersected by the projected triangles were marked. These marked voxels represented a discretization of the volume that should ideally be covered with the dwell segments. This is also known as the "pencil packing problem," for which finding an optimal solution is NP-hard (E. M. Arkin, S. P. Fekete, J. Kim, J. S. Mitchell, G. R. Sabhnani, and J. Zou, "The pencil packing problem," 2009). In one example, we suboptimally selected a set linear segments that cover the marked voxels (see Section VI for planned extensions to this step).

Figure 13:
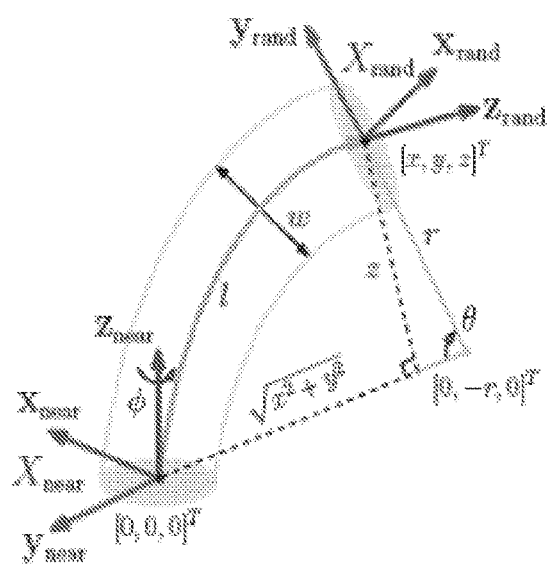
FIG. 13. The medial axis of each channel is parameterized with a sequence of circular arcs $\{\Psi_1, \Psi_2, \ldots, \Psi_n\}$. One such circular arc is shown parameterized as a tuple $[l, \phi, r]$. The channel is obtained by sweeping a disk of diameter w along the length of the arc. This arc connects the state $X_{near} \varepsilon SE(3)$ at the nearest tree node to the randomly sampled point $P_{rand} \varepsilon R^3$. It is assumed that the medial axis of the channel is oriented along the local z-axis at each point along the arc. The circular arc is constructed by rotating the local frame $X_{near}$ by an angle θ around a line parallel to the local x-axis and passing through the point $[0, -r, 0]^T$, $r > r_{min}$. The rotation φ rotates the tangential frame at the end of one circular arc to align it with the plane that contains the subsequent circular arc.

For each dwell segment D, a channel inside the implant volume was computed that reached it or a report that no channel was found was generated. The dwell segments were considered in decreasing order of distance from the entry region E. The medial axis of each curvature constrained channel was parameterized as a sequence of circular arcs $\{\Psi_1, \Psi_2, \ldots, \Psi_n\}$ in 3D space, where each circular arc $\Psi_1$ was parameterized as a tuple $[l_i, \phi_i, r_i]^T$ (FIG. 13). Here, $l_i$ is the length of the arc, $r_i > r_{min}$ is the radius of the arc, and $\phi_i$ is the twist applied to the tangential frame at the end of $\Psi_i$ that rotates the plane containing the arc $\Psi_i$ to the plane that contains the arc $\Psi_{i+1}$. The channel is constructed by sweeping a circle of diameter w along the medial axis.

Although the channels are constructed in 3D space, the state space of the layout problem comprises of both the 3D position and orientation (SE(3)) because of the constraints on the channel curvature. The position and orientation constraint at the end of each dwell segment d∈D can be described as $$X_d = \begin{bmatrix} R_d & p_d \\ 0 & 1 \end{bmatrix} \in SE(3)$$

comprising of the position $p_d$ of the end of the segment and rotation matrix $R_d$ encoding the orientation of the dwell segment in 3D. Without loss of generality, it was assumed that the dwell segment d was oriented along the z-axis of the local coordinate frame attached to the end of dwell segment.

Recent results in motion planning for nonholonomic systems emphasize sampling-based methods such as the Rapidly-exploring Random Tree (RRT) planner (S. M. LaValle, *Planning Algorithms*. Cambridge, U.K.: Cambridge University Press, 2006. Available at http://planning.cs.uiuc.edu) where the probability of finding a solution converges to one, if such a solution exists, as the number of samples approaches infinity. This approach was employed building on an algorithm to compute curvature constrained needle paths in 3D space (S. Patil and R. Alterovitz, "Interactive Motion Planning for Steerable Needles in 3D Environments with Obstacles," *Proceedings of the . . . IEEE/RAS-EMBS International Conference on Biomedical Robotics and Biomechatronics. IEEE/RAS-EMBS International Conference on Biomedical Robotics and Biomechatronics*, pp. 893-899, January 2010). Given a dwell segment d∈D, the planner was used to compute the medial axis of the channel while staying within the implant volume and avoiding obstacles and the set of existing channels C in the environment. The plan was formulated backwards starting from the dwell segment d to the entry region E because the larger entry region is less constrained.

Given initial state $X_d$ and entry region, the algorithm incrementally builds a tree X over the state space, while conforming to nonholonomic motion constraints of the system and avoiding obstacles. As described in Patil et al. (S. Patil and R. Alterovitz, "Interactive Motion Planning for Steerable Needles in 3D Environments with Obstacles," *Proceedings of the . . . IEEE/RAS-EMBS International Conference on Biomedical Robotics and Biomechatronics. IEEE/RAS-EMBS International Conference on Biomedical Robotics and Biomechatronics*, pp. 893-899, January 2010), building the tree in the SE(3) state space directly is computationally inefficient, so a random point $P_{rand} \varepsilon R^3$ was sampled, rather than a random state $X_{rand} \varepsilon SE(3)$. The planner then identified a node in the tree $X_{near}$ that was closest to the sample $P_{rand}$, as defined by a specified distance metric $\rho[\cdot]$. The sample $P_{rand}$ was then connected to $X_{near}$ using a circular arc parameterized by the tuple $[l, \phi, r]^T$. If the circular arc did not collide with the implant volume or existing channels and the minimum clearance from the obstacles is at least the channel width w, the arc was added as an edge in the tree. This process was repeated until either the tree X connects $X_d$ and E or the available computation time was exceeded, in which case the planner reported that a solution cannot be found. The medial axis of the channel was then be extracted from the tree by traversing backwards from the entry region to the dwell segment that corresponds to the root of the tree.

Random Point in $R^3(\cdot)$:

A random point $P_{rand} \varepsilon R^3$ was sampled within the implant volume I that is not collision with any of the channels in C. The sampled point was then connected to a given state $$X_{near} = \begin{bmatrix} R_{near} & p_{near} \\ 0 & 1 \end{bmatrix}$$

directly using a circular arc parameterized by $[l, \phi, r]^T$, where l is the arc length, $\phi$ is the change in orientation of the node $X_{near}$ around the $z_{near}$-axis, and r is the arc radius (FIG. 13). Let $[x, y, z]^T = R^T_{near}(P_{rand} - P_{near})$ be the coordinates of $P_{rand}$ in the local coordinate frame of $X_{near}$. The parameters of the circular arc were then given by:

$$r = \frac{x^2 + y^2 + z^2}{2\sqrt{x^2 y^2}} \quad (3)$$

$$\phi = \arctan(x, -y) \quad (4)$$

$$l = r \arctan(z, r - \sqrt{x^2 + y^2}). \quad (5)$$

To build toward the entry zone, two forms of biasing were incorporated when constructing the tree. First, the entry zone was sampled from a higher probability than the rest of the implant volume. Second, whenever a new node $X_{new}$ was added to the tree, the planner attempted to connect $X_{new}$ to a randomly sampled point in the entry zone E.

Nearest Neighbor(•):

The distance measure proposed by Patil et al. was used (S. Patil and R. Alterovitz, "Interactive Motion Planning for Steerable Needles in 3D Environments with Obstacles," *Proceedings of the . . . IEEE/RAS-EMBS International Conference on Biomedical Robotics and Biomechatronics. IEEE/RAS-EMBS International Conference on Biomedical Robotics and Biomechatronics*, pp. 893-899, January 2010) that is customized for nonholonomic systems with curvature constraints to select the tree node that was nearest to the sampled point $P_{rand}$. Since the channel had a minimum radius of curvature $r_{min}$, not all sampled points were reachable from a given state. The reachable set from a state $$X_{near} = \begin{bmatrix} R_{near} & p_{near} \\ 0 & 1 \end{bmatrix}$$

consists of all points that can be connected to $P_{near}$ by a circular arc that has a radius $r > r_{min}$ and is tangent to the $z_{near}$-axis of the local coordinate frame. This definition of the reachable set was used to define the distance metric $\rho[X_{rand}, P_{rand}]$ as the length of such a circular arc connecting $P_{rand}$ and $X_{near}$ if $P_{rand}$ was in the reachable set of $X_{near}$, and infinity otherwise.

$$\rho[X_{rand}, P_{rand}] = \begin{cases} l(\equiv r\theta) & \text{if } r \geq r_{min} \wedge \theta \geq 0 \\ \infty & \text{otherwise} \end{cases} \quad (6)$$

Circular Arc(•):

Given a circular arc parameterized as $[1, \phi, r]^T$ and a maximum step size $\Delta$ to progress at each iteration of the RRT algorithm, the position and orientation of the new node $X_{new}$ was computed by composing a rotation of $\phi$ around the $z_{near}$-axis and then applying a rotation of $\theta = \min\{1, \Delta\}/r$ around a line parallel to the xnear-axis and passing through the point $[0, -r, 0]^T$, $r > r_{min}$ in the local coordinate frame of $X_{near}$.

Collision Free(•):

To enable obstacle avoidance, only collision free arcs were added to the tree. Whether the circular arc connecting $X_{near}$ and $X_{new}$ is collision free was checked by approximating it as a sequence of line segments and checking if all the segments are collision free. Since the obstacle definitions were obtained from segmentation of 3D scans, the obstacle meshes were likely to be non-manifold. The SOLID library (G. van den Bergen, *Collision detection in interactive 3D environments*. Morgan Kaufmann, 2004) was used for detecting collisions with arbitrary, polyhedral obstacles at interactive rates. The minimum clearance of the circular arc was also checked to confirm it was at least the channel width w from the implant volume and existing channels to ensure that the channel that is constructed around the medial axis of this arc is collision free.

Permissible(•):

Since, in operation, the catheter carrying the source is inserted through the channels, it is preferred that the channel orientation at the entry region E is as close as possible to perpendicular to E. A cone of permissible orientations was allowed, i.e., the dot product of the local z-axis at a point on the channel medial axis at the entry region and the normal to the entry region should be less than the maximum allowable entry angle (deviation from normal), $\alpha$.

Build Channel(•):

A channel was found when the position $P_{new}$ of a newly added state $X_{new}$ was found to lie in the entry region E and the orientation $R_{new}$ was permissible. By traversing the tree X backwards from $X_{new}$ to the root $X_d$, a path was obtained composed of piecewise circular arcs $\{\Psi_1, \Psi_2, \ldots, \Psi_n\}$ constituting the medial axis of the channel, each with radius $r > r_{min}$. The channel was built by sweeping a circle of diameter w along the medial axis.

The channel was then added to the list of existing channels C and the process was repeated for the next most distant dwell segment until all dwell segments D are considered. As it was not always possible to find solutions for all dwell segments, a segment was reported as unreachable if a maximum number of iterations of the RRT algorithm are exceeded and no valid path was found to the entry region E. Alternate orderings of dwell segments can be utilized to produce better coverage and the present invention encompasses the use of such alternate heuristics.

Case Study and Evaluation

As a case study, a 3D model of OB/GYN anatomy with comparable scale and relative sizes of tumors and organs based on Barnhart et al. (K. T. Barnhart, A. Izquierdo, E. S. Pretorius, D. M. Shera, M. Shabbout, and A. Shaunik, "Baseline dimensions of the human vagina," *Human reproduction* (Oxford, England), 21:1618-22, June 2006) was considered. For this example, the diameter of the cavity near cervix is 50 mm and diameter at the vaginal introitus was 28 mm.

Three treatment methods were considered: standardized ring implant (current practice) (FIG. 14), customized 3D Printed implant with linear channels (FIG. 16), and customized 3D printed implant with curved channels (FIG. 15). These were compared with the coverage quality metric.

A standardized ring implant was first considered. The left image in FIG. 14 shows a ring implant placed in the vaginal cavity. The ring implant contains a toroidal channel running around the interior of the ring and number (usually 6) of parallel catheter channels running parallel to the axis of symmetry of the ring along near its outer diameter. A central tube (uterine tandem) passes into the uterine canal via the cervix. In a clinical procedure, the ring implant is inserted by the physician and then the patient is scanned using either MR or CT imaging. After scanning, a physician digitally segments the anatomical structures and digitizes the positions of the catheters. Using these structures and the set of catheter positions defined by their geometry, dose optimization software determines the best subset of dwell positions and times at each of these positions. The right image in FIG. 14 shows one such configuration of dwell positions superimposed on the implant.

Next an alternative was considered related to the plaster implant proposed by Magne et al. (N. Magné, C. Chargari, N. SanFilippo, T. Messai, A. Gerbaulet, and C. Haie-Meder, "Technical aspects and perspectives of the vaginal mold applicator for brachytherapy of gynecologic malignancies," *Brachytherapy*, 9(3):274-277, 2010), where the channels are manually created by the clinician by pushing linear catheters into the soft material. The right image in FIG. 16 shows a set of linear channels (skew lines) that reach as many of the dwell positions as permitted by the size of the entry zone.

Finally the implant with curvature-constrained non-linear channels generated by the CLA algorithm was considered: FIG. 15B.

The standardized ring implant can reach 18 potential radiation source dwell points, the 3D Printed implant with linear channels can reach 40 dwell points and the 3D Printed implant with curved channels can reach 149 dwell points. Table I lists the values of $\delta$ in mm at which coverage quality 2 reaches 100%. FIGS. 17A, 17B and 17C plot the quality metric for the three implant options (A), (B) and (C) as functions of coverage radius $\delta$ for 1, 5, 10, and 15 dwell points respectively.

TABLE 1

| | Implant Type | | |
| --- | --- | --- | --- |
| n multiple | Standardized Ring | 3D Printed with Linear Channels | 3D Printed with Curved Channels |
| 1 | 20.49 | 14.58 | 14.46 |
| 5 | 29.11 | 25.24 | 16.18 |
| 10 | 35.04 | 29.73 | 19.52 |
| 15 | 41.51 | 31.97 | 22.87 |

Discussion

The present invention provides a new approach to intracavitary brachytherapy using 3D printing and presents an algorithm for generating curvature-constrained internal non-linear channels. A case-study with an OB/GYN cervical and vaginal cancer compares three treatment options: standardized implant (current practice), customized implant with linear channels, and customized implant with curved channels. Results with a two-parameter coverage metric, summarized herein, suggest that customized implants with curved channels offer significant improvement over current practice. Such improvements in the coverage metric increase options for dose planning, which can reduce occurrence of hot spots and increase dose conformality to the tumor geometry to spare healthy tissue.

Example 2

This Example illustrates the 3D printing of an exemplary device of the invention . . . . The patient had cancerous tumors on cervix and vaginal wall.

I. Patient Scan and Physician Contouring

Anonymized patient data from the UCSF patient database was used for this study. The patient, Anon1, was scanned with CT-Scan and found to have cervical cancer. In the clinic, Anon1 was treated using a commercially available, non-customized (standard shaped) Interstitial Ring. In this case study an alternative approach is developed which replaces the Interstitial Ring with a custom implant that is contoured to patient anatomy and includes curved interior channels that can guide radioactive sources to deliver radiation closer to tumors and with more accuracy than with standard Interstitial Ring methods.

Anon1 had been scanned using a CT-scanner and anatomical images were generated as slices in axial, coronal, or sagittal planes. (The CT-Scanner usually takes one helical scan which is then generally viewed in three planes). UCSF Dept. of Radiation Oncology uses Oncentra, proprietary software from Nucletron™. Oncentra is used of displaying and interacting with CT-scan data.

A clinician then manual contours the boundary of organs and tumors on selective image slices in axial plane in Oncentra. In case of Anon1, the following structures were contoured: Urinary Bladder, Rectum, Tumor Volume, Vaginal Cavity and the Ring in the applicator used for treatment.

In case of Anon1, the anatomy has following volumes (in $cm^3$):

| | |
|---|---|
| Urinary Bladder: | 86.22 $cm^3$ |
| Rectum: | 175.81 $cm^3$ |
| Tumor: | 84.935 $cm^3$ |
| Vaginal Cavity: | 104.94 $cm^3$ |

This data was output as a set of images (DICOM) and description files for organ contours (RTSTRUCT). These are standard formats for storing and transmitting medical image data. The copyright for DICOM is held by National Electrical Manufacturers Association, the details of which are listed in http://dicom.nema.org/.

II. Create 3D Volumetric Model of Anatomy

After initial scanning, CT Scan data was stored in DICOM files and all organ contours were marked in the data and stored in a RTSTRUCT database. The size of this database was 54 megabytes.

Thereafter, Slicer3D, an open-source software created by researchers at Harvard (Fedorov A., Beichel R., Kalpathy-Cramer J., Finet J., Fillion-Robin J-C., Pujol S., Bauer C., Jennings D., Fennessy F., Sonka M., Buatti J., Aylward S. R., Miller J. V., Pieper S., Kikinis R. 3D Slicer as an Image Computing Platform for the Quantitative Imaging Network. Magn Reson Imaging. 2012 November; 30(9):1323-41. PMID: 22770690; http://www.slicer.org/), was used for further data processing. Slicer3D has very similar capabilities as Oncentra.

Slicer3D can directly import DICOM images. Additionally, a plugin for Slicer3D called SlicerRT allows reading RTSTRUCT files along with the DICOM files. Imported organ contours were overlaid on the three image planes, as they were in Oncentra.

Slicer3D by default displayed a Ribbon Model of the anatomy, wherein discontinuities in the organ volumes were clearly visible. Since the organ contours were drawn only on selective slices, hence there was a need for reconstructing the closed volumes from the contours.

Using the Contours package in Slicer3D, the anatomy representation was converted from the Ribbon Model to Closed Surface Model (http://wiki.slicenorg/slicerWiki/index.php/Documentation/4.2/Modules/Contours). During this conversion, default parameter settings were used: oversampling rate of 2 and target reduction of 0%. This conversion resulted in a closed volume model of all the relevant anatomical structures.

Slicer3D can output closed anatomy volumes in several commonly used mesh formats (.stl, .ply etc.). STL were chosen as preferred format. STL files are human readable specification of the mesh files in terms of triangles and surface normal vectors. Most 3D printers accept .stl files for printing structures.

A separate mesh file for each organ was then created and saved.

III. Create and Clean Cavity and Tumor Meshes

Slicer3D volume reconstruction resulted in non-smooth surface. This step can be improved in the future with the use of a better volume reconstruction algorithm than the default provided by Slicer3D.

The output meshes also had a similar non smooth texture as did the reconstructed volumes in Slicer3D. An opensource software MeshLab was used for mesh editing. It has been under development since 2005 with support of 3D-Co-Form (http://meshlab.sourceforge.net/). Tumor and Vaginal cavity meshes were imported into MeshLab.

Mesh smoothing process required using a combination of algorithms provided in Meshlab list of Filters. A combination of Laplacian smoothing and MLS (moving least square) Projection using Algebraic point set surfaces (Guennebaud, G., & Gross, M. (2007, August), Algebraic point set surfaces. In *ACM Transactions on Graphics (TOG)* (Vol. 26, No. 3, p. 23). ACM). This results in smooth meshes of both tumors and cavity.

Furthermore, to make the example sufficiently complex for planning channels, another tumor was added near the side wall of the cavity. This tumor was a free-form closed volume designed using commercial CAD software (SolidWorks™). Solidworks version 2013 was used for all CAD requirements for this case study.

This tumor is designed in manner that is shares the same coordinate frame as the vaginal cavity and the existing tumor so as to eliminate registration problems.

The CAD software can export a smooth .stl mesh file for the new tumor in the same coordinate reference frame.

IV. Planning Channels: First Step: Specify Dwell Segments

Thereafter, the locations of dwell segments in the vaginal cavity were specified. These dwell segments would 'cover' the tumors and also minimize radiation to vaginal wall. In the current iteration these dwell segments were specified manually.

A commercially available CAD software, SolidWorks 2013 was used to load the tumor meshes and the vaginal cavity mesh. The meshes were loaded in SolidWorks and aligned to same coordinate frames (give details). Each mesh was imported as a surface body using the same scale (in mm) as of the STL file. No texture information was loaded.

Thereafter, the projection of the tumors on the vaginal cavity was noted by visual inspection in the 3D viewing interface of Solidworks. The meshes of different organs were displayed in different translucent colors to enable this visual inspection. Thereafter to mark dwell segments, multiple reference planes were created in the vaginal cavity. These planes were created in a manner that: a) they were parallel to a surface triangle which lied proximal to the tumor and b) they were in the cavity by at least 3.5 mm. The 3.5 mm margin was to ensure that the dwell segment would remain in the cavity at all times.

Each dwell segment was drawn as a reference line segment on the reference planes drawn earlier. The dwell segments were specified as end points of these reference line segments, with each dwell segment lying on a reference plane closest to the surface, covering the tumor projection (visual confirmation), and lying completely within the vaginal cavity.

At the end of marking all dwell channels required for this procedure, the dwell segments were output as a list of tuples each containing start and end points for each dwell segment. These were stored in a text file (.txt)

Dwell segments are optionally computed by other geometric algorithms.

V. Computing Treatment Delivery Channels

The input to channel planner took in vaginal cavity mesh (.stl file) and specification of target dwell segments (.txt file). The mesh for the vaginal cavity as created earlier was a closed volume. Meshlab was used for slicing the vaginal cavity mesh. In this step, the cavity mesh was opened up at the bottom by deleting triangles from the bottom surface. Meshlab allows selecting specific triangles in a mesh and operating on them. For mesh slicing, triangles located on the bottom face were selected manually. These triangles were successively deleted until a hole of sufficient diameter was obtained.

This operation is optionally performed by using a more sophisticated mesh editing tool and performing a slicing operation (intersect a mesh with a plane).

Thereafter, the open mesh file and the dwell segments are loaded in research code for handling channel planning. The code is written in C++. A planar entry zone with circular section is created sufficiently below the cavity mesh, to allow for channels to be planned beyond the cavity wall. The reasons for this choice will be made clear in following sections. The channel planning algorithm is described in the paper by Garg et al (Garg Animesh, Sachin Patil, Timmy Siauw, J. Adam M. Cunha, I-Chow Hsu, Pieter Abbeel, Jean Pouliot, and Ken Goldberg. "An Algorithm for Computing Customized 3D Printed Implants with Curvature Constrained Channels for Enhancing Intracavitary Brachytherapy Radiation Delivery." Accepted for publication in *IEEE International Conference on* In *Automation Science and Engineering (CASE)*, IEEE, 2013).

The parameters settings are: 1) channel diameter: 3.5 mm; minimum curvature: 0.5 mm; and number of channels: 11.

The choice of channel diameter and minimum curvature was made based on empirical evidence. A test implant with channels of varying diameter and a range of curvature was created. The diameter was chosen from a set of $\{2, 3, 3.5, 4\}$ mm. Minimum Curvature was chosen from the set $\{10, 7.5, 5, 2.5\}$ mm. 16 channels with all combinations of diameter and minimum curvature settings were printed in a test implant. A physical version of this implant was created using 3D printing. Thereafter tests with brachytherapy catheters (2 mm outer diameter) were performed to find out the best channel parameters which could accommodate the catheter without inducing kinks or breaking it.

The choice of number of channels in this case study was largely dependent on manual specification of dwell segments. Only 11 dwell segments were specified, hence 11 channels were used. Furthermore, the user decision to mark only 11 channels was also in part driven by the diminishing efficacy of adding more channels and also increasing interference at the cavity surface near the tumor.

For every dwell segment, the output of the channel planning algorithm gave a path from the proximal end of the dwell segment to the circular entry zone. The path was specified as a sequence of points. In this example, feasible paths for all 11 channels which fit inside the vaginal cavity were successfully found. Each channel was completed by connecting the path from proximal end to the distal end of the dwell segment, using smooth interpolation between the two end points and then sampling points along the interpolated line. Hence each channel in the planner output connected the distal end of the dwell segment to a point in the entry zone.

It was noted that in this case, both for illustrative purposes and to facilitate fabrication in the 3D printer, dwell segments were extrapolated to exit the implant surface. This allowed each channel in the final implant to have an opening at the implant surface beyond the distal end. This distal opening could later be plugged before actual treatment procedure.

At the end of channel planning, the list of paths is output. Every channel, represented as a path was output as list points along the path. The output is in the form of a comma separated values (text file) with each line containing a tuple for a point in 3D Cartesian coordinates.

VI. Construct Mesh for Continuous Cylindrical Channels

Given the list of points for each channel path, a smooth channel mesh could be constructed. This was facilitated by sliding a circular profile along a smooth spline constructed with points on the path.

This operation could have been done programmatically with use of existing surface generation techniques. However, use of SolidWorks 2013 CAD software was preferred to minimize implementation effort at design stage. A more robust implementation could potentially use custom designed code.

A cylindrical channel was created in following steps:
1. The list of points along the path for each channel were imported.

2. A smooth spline was created using the points as seeds using the parameter free 'Curves through XYZ point' function in Solidworks.

3. Two circular cross-sections of diameter 3.5 mm centered at end point of the spline curve path were created. Furthermore it was ensured that the cross sections were in a plane normal to the spline curve at end points.

4. The two cross-sections were connected with circular profile running along the spline as guide curve. This was performed using a Loft Boss/base operation in Solidworks. The circular profiles were specified as start and end profiles, while the spline was specified as the guide curve.

Start and end constraints on the guide curve were set to be normal to the profile. It was also ensured that the resultant profile had minimum torsion connection and also maintained a constant diameter throughout. Also the checkbox 'merge tangent faces' was checked (by default) during the Loft Boss/Base operation.

Cylindrical channels were created for all 11 channels in the same coordinate frame in the same CAD file. Thereafter the set of all channels was output in a single .stl file. This file was essentially a triangulation of each cylindrical channel with surface normal vectors facing outwards.

VII. Create Final Implant

With the mesh of all the channels created, it was to be combined with the original closed vaginal cavity mesh. Mesh difference operation in the MeshLab under the CSG filter with default parameters was used. The parameters were: (a) Space between sampling lines: 1% (0.4624), (b) Discretization points per sample interval: 32, (c) Using Extended Marcing Cubes Algorithm (checkbox ticked) and (d) Operator: Difference. Hence, the mesh of channels was subtracted from the vaginal cavity mesh leaving behind a cavity mesh only with hollow channels.

VIII. 3D Print Implant

The final mesh in .stl format can be exported to any standard 3D Printer. A uPrint SE Plus from StrataSys Inc. was used for this case study. The printer specifications are available at the StrataSys Inc. website (http://www.stratasys.com/3d-printers/idea-series/uprint-se-plus; http://www-.stratasys.com/3d-primers/idea-series/~/media/ 854AB84DCADB4D48A55F539CF321FEC6.ashx). The printer can print at a variable resolution of either 0.01 in (254 µm) or 0.013 in (330.2 µm).

The implant was printed with commercially available ABS Plastic material, with a layer resolution of 234 µm. Each part took approximately 6 hours to print. Thereafter the part needed to be agitated in a solution tank with sodium hydroxide solution to dissolve the support material printed with the part. The normative time for the latter procedure was 4 hours.

It is worth noting that a mid-range printer was used for producing this part. However other higher quality printers were also explored which could print at a resolution of 16 µm and also decrease the total build time by three fold. (http://www.3dsystems.com/3d-printers/professional/projet-3500-cpxmax).

IX. Checks on Printed Implant and Quality Measure

To confirm that all the channels were clear of support material and printing (and other building) defects, the following procedure was adopted:

1. The length of the channel was measured along the spline from start to end;
2. This length was marked on the catheter using a rubber stopper;
3. The catheter was then inserted in the channel;
4. If the Catheter didn't reach the end, the rubber stopper would not reach the proximal opening of the channel on the implant surface. Thereafter, we would conclude either the channel is blocked (due to deposition of support material from 3D printing) or the catheter couldn't be pushed in until the intended length.

The same steps 1-4 were repeated for all catheters.

Example 3

Clinical Applications of Custom-Made Vaginal Cylinders Constructed Using 3D Printer Purpose:

3D printing technology allows physicians to rapidly create highly customized devices for patients. This technology has already been adapted by various fields in medicine. We report a proof of concept and first clinical use of this technology for vaginal brachytherapy.

Introduction:

There are currently many medical applications of 3D printing in development, for example, medical modeling for maxillofacial surgical management (Chow, et al., *Journal of Oral and Maxillofacial Surgery*, 65(11):2260-2268, 2007; Anchieta, et al., *Advanced Applications of Rapid Prototyping Technology in Modern Engineering*. Rijeka, Croatia: InTech, pp. 153-72, 2011), bone reconstructions (Cohen, et al., *Oral Surgery, Oral Medicine, Oral Pathology, Oral Radiology, and Endodontology*, 108)(5):661-666, 2009; Schrank, et al., *Journal of Biomechanical Engineering*, 135(1):101011, 2013), and oral surgeries (Winder, et al., *Journal of Oral and Maxillofacial Surgery: Official Journal of the American Association of Oral and Maxillofacial Surgeons*, 63(7):1006, 2005). The precision of 3D printers has been closely evaluated for medical applications with several studies confirming high levels of precision (Winder, et al., *Journal of Medical Engineering & Technology*, 23(1): 26-28, 1999; P. Webb, *Journal of Medical Engineering & Technology*, 24(4):149-153, 2000). There is published interest in 3D printing for brachytherapy (Poulsen, et al., *International Journal of Radiation Oncology Biology Physics*, 44(3):731-735, 1999; Pompeu-Robinson, et al., *International Journal of Computer Assisted Radiology and Surgery*, 7(1):65-72, 2012; Mutic, et al., *International Journal of Radiation Oncology Biology Physics*, 52(4):1104-1110, 2002; Maalej, et al., *Cancer/Radioth'erapie*, 11(3):117-121, 2007; Makni, et al., *Prostate Cancer Imaging. Image Analysis and Image-Guided Interventions*, pp. 22-34, 2011) and discussion of its use to construct custom GYN applicators (Albano, et al., *Cancer Ra-diother*, 12:822-6, 2008; Wiebe, et al., *Cancer/Radioth'erapie*, 12:822, 2008).

Manufacturers have supported medical interests in 3D printing by introducing printing materials that pass the International Standard ISO-10993 as well as the United States Pharmacopeia standards for biocompatibility (Novakova-Marcincinova, et al., *Advanced Materials Research*, 740:597-602, 2013). PC-ISO is both USP Class VI approved and ISO-10993-1 rated. The material is also sterilizable and has high flexural and tensile strength properties that have made it a common choice for many medical applications (Novakova-Marcincinova, et al., *Advanced Materials Research*, 740:597-602, 2013; Koo, et al., *The International*

*Journal of Artificial Organs*, 33(10):731, 2010; Hitch, et al., "Assessment of a virtual functional prototyping process for the rapid manufacture of passive-dynamic ankle-foot orthoses". For example, PC-ISO has been explored for use in ankle-foot orthoses (Schrank, et al., *Journal of Biomechanical Engineering*, 135(1):101011, 2013), lumbar cages (Aherwar, et al., *High Value Manufacturing: Advanced Research in Virtual and Rapid Prototyping: Proceedings of the 6th International Conference on Advanced Research in Virtual and Rapid Prototyping*, Leiria, Portugal, 1-5 October, 2013. CRC Press, 2013, p. 345), and bone screw linking devices (Groscurth, et al., "Bone screw linking device," Sep. 15, 2010, U.S. patent application Ser. No. 12/882,800).

In an effort to improve applicator fit and resulting implant geometry, we used three-dimensional printing technology as a way to manufacture customized brachytherapy applicators for women undergoing vaginal brachytherapy. Poor applicator fit during vaginal intracavitary brachytherapy can lead to air gaps and under-dosing of the target volume. For interstitial implants, poor applicator fit may lead to poor implant geometry and increase inter-fraction variability when multiple fractions are delivered over a single implant. While commercial applicators are available in a variety of sizes, we desired further flexibility in applicator shape and structure to improve fit within a cavity or allow optimal needle positioning for interstitial technique. While other centers have documented interest in personalized vaginal applicators, we know of no prior experience using three-dimensional printing to this end. In this example, we report on the first two patients treated with three-dimensional printed applicators at our institution, after receiving institutional review board approval. The first is a case of adjuvant intracavitary vaginal cuff brachytherapy for endometrial cancer, and the second is a case of interstitial brachytherapy and hyperthermia for a vaginal cuff recurrence of endometrial cancer.

Methods and Materials:

There were multiple steps in creating a workflow to enable use of this technology in the clinic. To design the applicator, we created multiple prototypes based on measurements from existing vaginal cylinders using computer aided design (CAD) software (Autodesk, Inc., San Francisco, Calif.). These prototypes were printed on non-medical grade plastic material. Once we developed the designing workflow, we determined which plastics could be printed and sterilized, and we identified a printing facility that could accommodate those materials. Documentation was obtained of an independent study describing the effectiveness of the STERRAD sterilization system for use with the thermoplastic we chose (PC-ISO; Stratasys, Eden Prairie, Minn.). Multiple quality assurance and physical evaluations were performed on several prototypes to ensure that the applicator was suitable for clinical use, which will be reported in a separate technical paper. After achieving all of these tasks, we were able to build the first custom applicators for clinical use in the following patients.

Patient 1:

Patient 1 is a 56 year-old woman with stage IA serous endometrial cancer who was referred for vaginal cuff brachytherapy following chemotherapy. Based on physical examination and measurements at the time of consultation, the optimal applicator size was determined to be a 2.75 cm diameter vaginal cylinder. Since the vaginal cylinder applicators at our institution are available only in 2.5, 3, or 3.5 cm diameter sizes, we therefore decided to produce a custom-sized applicator using three-dimensional printing technology to better fit this patient's anatomy.

Figure 33A:
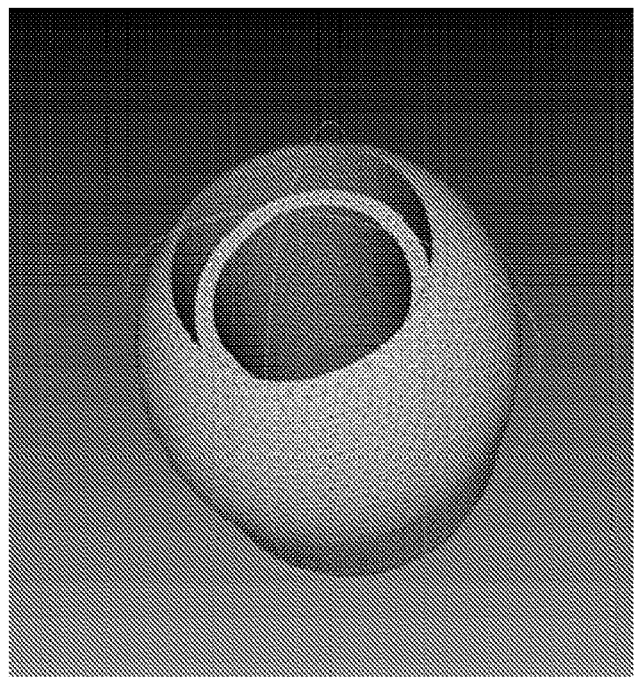
FIGS. 33A-B are 3D renderings and the custom printed cylinder for segmented cylinder with 2.75 cm diameter.
Figure 33B:
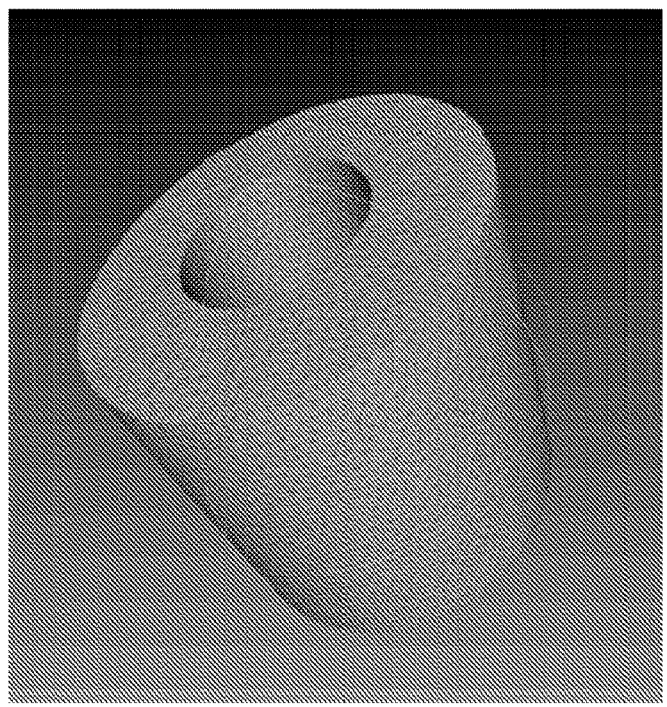

We used CAD software (Autodesk, Inc., San Francisco, Calif.) to design a 2.75 cm diameter segmented cylinder with a single central channel, scaled from a commercially available applicator that we routinely use for HDR brachytherapy treatment. The cylinder was printed on a Fortus 400 mc (Stratasys Ltd., Eden Prairie, Minn.) three-dimensional printer, using PC-ISO biocompatible thermoplastic (Stratasys Ltd., Eden Prairie, Minn.) (FIG. 33). The thermoplastic cylinder was sterilized using a STERRAD (Ethicon, Inc., Sommerville, N.J.) sterilization system.

At the time of treatment, 2 fiducial gold markers were inserted into the vaginal cuff apex prior to the first insertion. The sterilized cylinder was inserted into the vagina, and the position was verified on scout film. CT images of the treatment area were obtained, and the applicator and organs at-risk were contoured on Elekta-Nucletron Oncentra Planning System. Three-dimensional inverse planning (IPSA) was used to develop a treatment plan to deliver 31.5 Gy over 3 fractions of 10.5 Gy per fraction, prescribed to the surface of the vagina. The applicator surface was used as a proxy for vaginal surface for the purposes of treatment planning. The IPSA class solution was designed with the goal of achieving 10.5 Gy to the surface of vagina. The length of vagina treated was based on physician's contour. Coverage was verified by visual confirmation of the confluence of the 10.5 Gy isodose surface with the applicator surface. 3D volumetric doses were calculated for the bladder, rectum, bowel and the target volume. The treatment was delivered using Elekta-Nucletron remote afterloader.

Figure 34A:
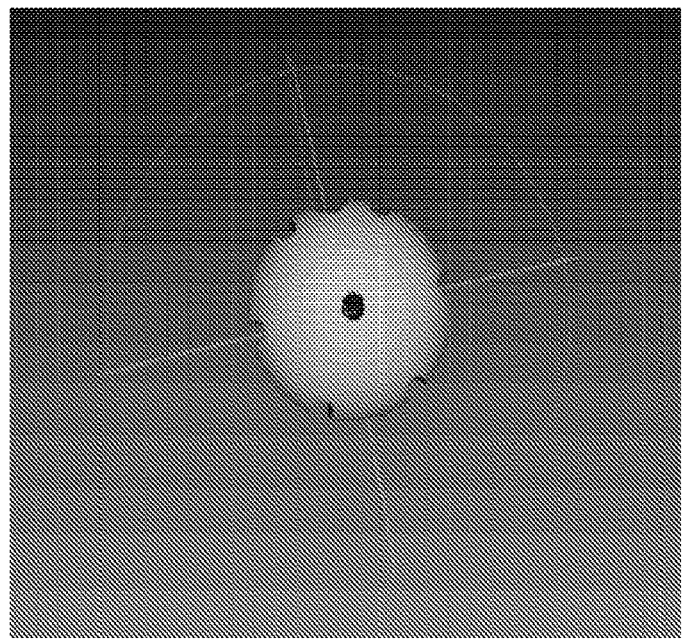
FIGS. 34A-B are 2 cm diameter custom printed cylinders with external and central catheter channels for use in interstitial brachytherapy and hyperthermia in a patient with very narrow vaginal vault after prior surgery and radiation.
Figure 34B:
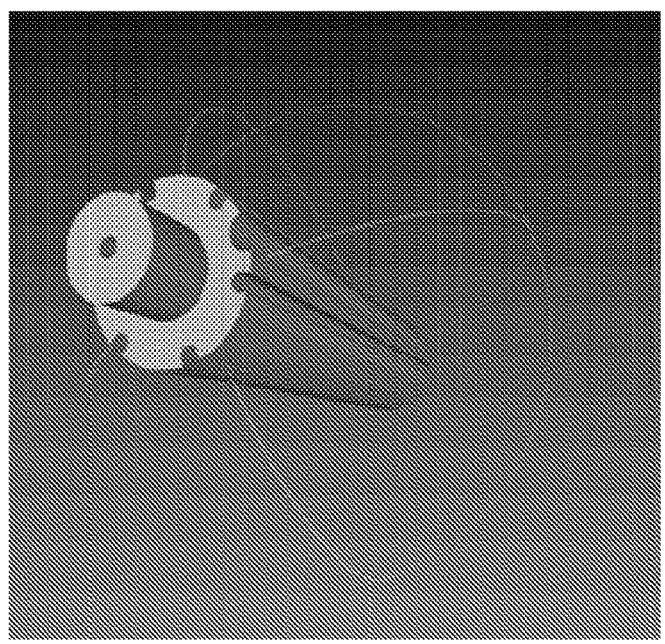

Patient 2:

Patient 2 is a 67-year-old woman with vaginal cuff recurrence of stage IA grade 1 endometrioid endometrial cancer who had initially undergone total abdominal hysterectomy, bilateral salpingo-oophorectomy showing inner half myometrial invasion, grade 1 disease, and no lymphovascular invasion, who subsequently developed a vaginal cuff recurrence and was treated with whole pelvis external beam radiotherapy to a dose of 45 Gy, followed by vaginal cuff brachytherapy to a dose of 15 Gy over 3 fractions. She later developed a second vaginal cuff recurrence as well as distant metastatic disease and was referred for palliative brachytherapy to the vaginal cuff lesion, which was painful and bleeding. Due to her prior treatment, the vaginal canal was very stenotic, and our narrowest commercial applicator could not be comfortably inserted. We therefore decided to print a vaginal cylinder applicator, of 2 cm diameter, with a central catheter channel as well as six evenly spaced longitudinal surface grooves for interstitial brachytherapy to the vaginal cuff (FIG. 34). We used the same printing process and equipment as described for Patient 1.

At the time of treatment, two marker seeds were placed at the vaginal cuff. The patient underwent trans-rectal ultrasound (TRUS)-guided interstitial brachytherapy. During this procedure, multiple 30-cm interstitial catheters are inserted lateral to the introitus parallel to the vaginal using TRUS guidance. Additional catheters were inserted into the superficial and central grooves on the vaginal cylinder and advanced superiorly into the tumor under TRUS guidance. The cylinder was secured to the vagina using sutures and the catheters to the cylinder using dental putty. The final implant consisted of 9 interstitial catheters. The patient received 36 Gy over 2 implants, with 6 Gy per fraction and 3 fractions per implant prescribed to the GTV. CT-simulation and inverse planning was used using pre-operative MRI scan to guide tumor delineation. The GTV, bladder, rectum, and bowel were contoured. As with Patient 1, IPSA was used for planning. The IPSA class solution was designed to maximize the volume of the GTV receiving the at least the prescription dose, minimize hotspots in the GTV (V150%), and keep the V75% of the bladder, rectum, and bowel below 1 cm³.

This particular patient also received two interstitial hyperthermia treatments, once during each implant. Hyperthermia was delivered using the BSD 500 System, with MA-251 interstitial microwave antenna and temperature monitoring sensors inserted within selected implant catheters (BSD Medical Corporation, Salt Lake City, Utah). Target temperatures of 39.5-45° C. for 60 min were administered immediately following treatment of either the first or second brachytherapy fraction. Hyperthermia treatment parameters include 4-5 microwave antenna with 4-6 W applied power per antenna, and four temperature sensors within adjacent catheters.

Figure 35:
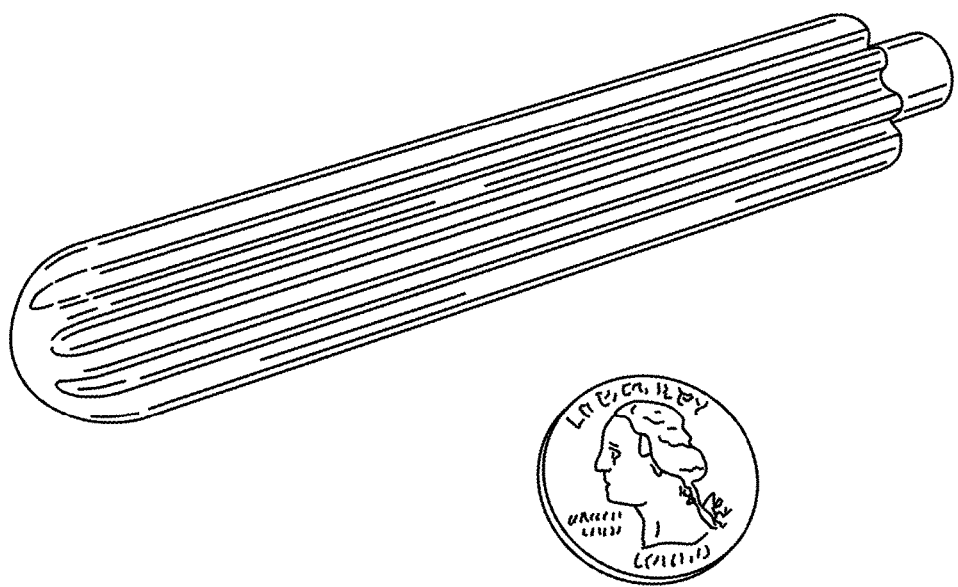
FIG. 35 provides axial, sagittal, and coronal views of the brachytherapy treatment plan for Patient 1.
Figure 36:
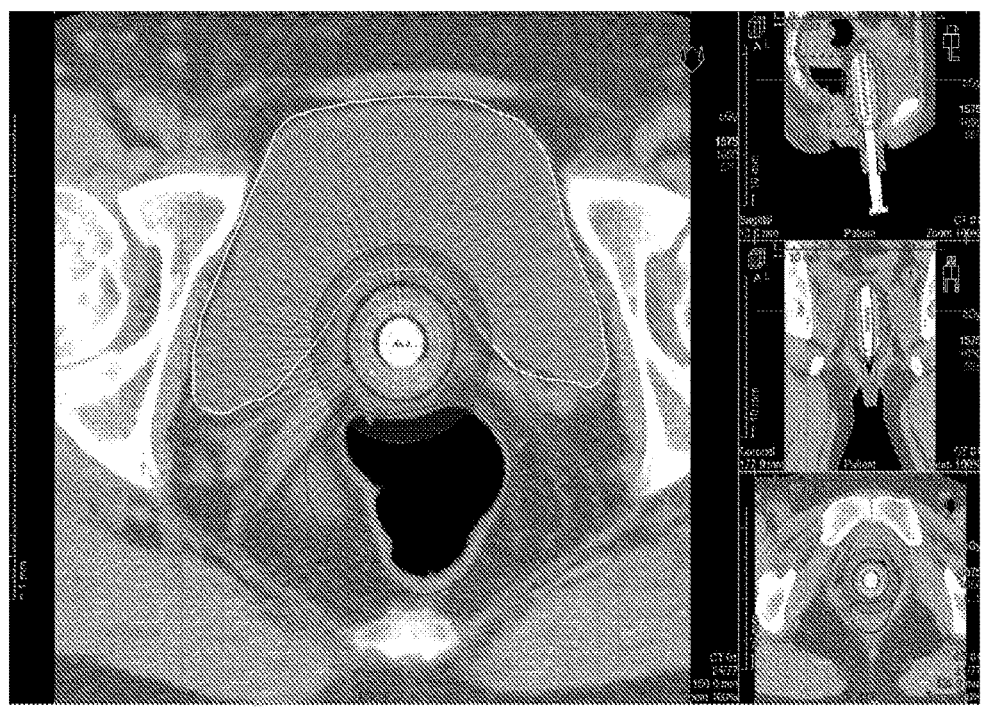
FIG. 36 shows axial, sagittal, and coronal views of the brachytherapy treatment plan and interstitial catheters for Patient 2. Hyperthermia was delivered sequentially after a single fraction with interstitial microwave antenna and monitored with temperature sensors in the distal segments of the implant catheters positioned within the CTV.

Results:
Patient 1:

Radiotherapy was delivered without complications. The patient tolerated the 2.75 cm cylinder without discomfort, and there were no air-gaps seen at the time of CT-simulation. The plan is depicted in FIG. 35. DVH parameters were as follows: bladder V75%=0.01 cc, V85%=0 cc, D2 cc=6.53 Gy; rectum V75%=0.95 cc, V85%=0.06 cc, D2 cc=7.31 Gy; bowel V75%=0 cc, V85%=0 cc, D2 cc=4.68 Gy; CTV V100%=90%. The patient experienced no acute treatment effects of treatment other than mild fatigue for two weeks. After nine months of follow-up, she had no evidence of disease on exam, although she had several adhesions at the vaginal apex.

Patient 2:

Interstitial brachytherapy and hyperthermia were delivered without complications. DVH parameters were as follows: bladder V75%=0.24 cc, V85%=0.01 cc, D2 cc=3.80 Gy; rectum V75%=0.24 cc, V85%=0 cc, D2 cc=3.69 Gy; bowel V75%=0.4 cc, V85% 0 cc, D2 cc=3.24 Gy; GTV V100%=91%.

Hyperthermia treatment 1 was delivered as prescribed using four interstitial applicators, with 4-6 W power applied to each antenna, generating target temperatures between 40-43.9° C. for 60 min duration, and thermal dose between 1-49 $EM_{43° C.}$ (Equivalent Minutes at 43° C.). Hyperthermia treatment 2 utilized five interstitial applicators, with 4.5-5.5 W applied power, with temperatures of 39.4-44.8° C. and thermal dose 2-28 $EM_{43° C.}$ achieved.

The patient experienced fatigue and clear vaginal discharge for one month after treatment, and had cessation of bleeding and resolution of pelvic pain at her three-month follow-up visit. CT of the pelvis at that time showed reduction in size of the vaginal tumor.

DISCUSSION AND CONCLUSIONS

We established the clinical feasibility of using 3D printed applicators for vaginal brachytherapy. We have found these applicators useful for women whose anatomy falls outside the range of commercial applicators. In particular, Patient 2 would not have been able to tolerate even the smallest commercial applicator (2.5 cm diameter), and the printed applicator (2.0 cm diameter) made her implant feasible. In order to clinically implement these applicators while ensuring patient safety, multiple challenges in the design, manufacturing, and clinical application needed to be addressed.

With respect to applicator design, one challenge with our current process is the process of estimating fit, which is currently based on physical exam to estimate the dimensions of our diameter. Imaging assists in the selection of dimensions for more accurate fit and to potentially allow construction of abstract-shaped applicators to fit non-uniform cavity shapes.

The manufacturing process posed several challenges as well. A suitable material needed to be selected and subjected to multiple quality assurance tests to document its feasibility for clinical use. Namely, the thermoplastic we selected was preferably biocompatible, sterilizable, CT-compatible, and have similar dose-attenuation properties to water in order to be compatible with our brachytherapy planning system. We selected PC-ISO because (1) it has International Standard ISO-10993 Class VI Certification for biocompatibility, meaning it is FDA approved for temporary skin contact (Novakova-Marcincinova 2013, Schrank 2013) and (2) it is sterilizable (Perez 2012). In addition, we have conducted a series of quality assurance tests to ensure its safe clinical use, which will be published elsewhere.

The clinical application of these cylinders went smoothly and resulted in high quality implants with good patient comfort. A drawback that was noticed during the planning process for Patient 1 is that the density of PC-ISO is virtually tissue-equivalent on CT. This made applicator delineation more difficult with CT-based planning, particularly for Patient 1. This can be addressed by changing the density at which the thermoplastic is printed or by placing, a small amount of contrast between the cylinder and condom cover prior to insertion at the time of simulation. The latter is viable for patients undergoing intracavitary treatments using a vaginal cylinder with a single central channel and no interstitial catheters. This was not a problem for Patient 2, because the peripheral catheters were useful to delineate the surface of the cylinder.

In summary, the present study used three-dimensional printing technology to print custom applicators for patients undergoing gynecologic brachytherapy, and which resulted in high-quality implants. 3D printing can enable production of applicators with excellent fit and optimized interstitial needle placement to enable target coverage, normal tissue sparing, and implant stability.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A removably implantable device customized to be positioned proximal to an internal surface of a body cavity of a subject in which said device is implanted, said device configured to provide localization of at least one local means of tumor control to a diseased tissue of said subject proximate to said body cavity, said device comprising:
    a device body comprising an exterior surface configured to contact said internal surface of said body cavity, and an internal region having at least one curvature constrained channel disposed therein, said at least one curvature constrained channel being configured to accept said at least one local means of tumor control, and comprising at least one opening communicating with said external surface
    wherein at least one zone of said device body comprises a shielding material capable of essentially blocking an effect from said at least one local means of tumor control disposed within said at least one curvature constrained channel.

2. The device according to claim 1, further comprising said at least one local means of tumor control, said at least one local means of tumor control is disposed within said at least one curvature constrained channel.

3. The device according to claim 1, wherein said at least one local means of tumor control is a member selected from a chemotherapeutic agent, a source of cold, a source of ionizing radiation, a source of heat, a source of light, and a combination thereof.

4. The device according to claim 1, wherein said at least one local means of tumor control is removably insertable into said at least one curvature constrained channel.

5. The device according to claim 1, configured such that said at least one local means of tumor control is removably insertable from outside said body of said subject after said device is implanted in said body cavity of said subject.

6. The device according to claim 1, wherein said at least one local means of tumor control is disposed within said device at a site selected such that, when the device is implanted in said body cavity of said patient, said at least one local means of tumor control is registered with said diseased tissue to be treated by said local means of tumor control.

7. The device according to claim 6, wherein said device is configured to direct said at least one local means of tumor control towards said diseased tissue.

8. The device according to claim 7, wherein said device is configured such that less normal tissue of said subject proximate to said diseased tissue is ablated than would be ablated by an identical therapeutically effective amount of said local means of tumor control administered in the absence of said device.

9. The device according to claim 1, wherein said shielding material is disposed at a member selected from said internal region, said at least one curvature constrained channel, said exterior surface, a region between said curvature constrained channel and said exterior surface, and a combination thereof comprises a shielding material capable of shielding tissue of said subject from said at least one local means of tumor control.

10. The device according to claim 1, wherein said shielding material is a material selected from a liquid and a solid.

11. The device according to claim 1, having at least two said curvature constrained channels and none of said at least two curvature constrained channels intersect.

12. The device according to claim 1, having no channels that are linear channels.

13. The device according to claim 1, wherein said device is formed from a material capable of being 3-D printed.

14. The device according to claim 13, wherein said material is an organic polymer.

15. The device according to claim 13, wherein said material is permeable to light of a frequency appropriate for phototherapy, conducts heat, allows the passage of ionizing radiation and a combination thereof.

16. The device according to claim 13, wherein said, device is formed by 3-D printing of said device.

17. The device according to claim 1, wherein said device further comprises one or more imagable fiducial marker(s) configured for registration between at least one region of anatomy of said subject and at least one diagnostic image of said region of anatomy.

18. The device according to claim 17, wherein said region of anatomy comprises said diseased tissue.

19. The device according to claim 17, wherein said one or more imagable fiducial marker(s) is acquired by a modality selected from MRI, CT, gamma camera scintigraphy, PET, ultrasonography and a combination thereof.

20. The device according to claim 17, wherein said one or more imagable registration fiducial marker(s) is imageable by a modality selected from MRI, CT, gamma camera scintigraphy, PET, ultrasonography and a combination thereof.

21. The device according to claim 1, wherein said internal region is substantially solid, with an exception of said at least one curvature constrained channel, which is substantially hollow.

22. The device according to claim 1, wherein said internal region is substantially hollow, with an exception of said at least one curvature constrained channel, which is a luminal structure disposed within the substantially hollow internal region and anchored to a first position and a second position of a surface of said internal region.

23. The device according to claim 22, wherein said at least one local means of tumor control is a radioactive source.

24. The device according to claim 1, wherein said at least one local means of tumor control is disposed at a position within said at least one curvature constrained channel, forming a dwell point.

25. The device according to claim 1, wherein said disease is neoplasia.

26. A method of treating a neoplastic disease in a patient in need of treatment thereof, said method comprising: implanting said device according to claim 1 in said body cavity of said subject such that a therapeutically effective dose of said at least one local means of tumor control is delivered to a locus of said neoplastic disease from a dwell point in said device.

27. The method according to claim 26, wherein said therapeutically effective dose of said local means of tumor control is delivered to said locus of neoplastic disease from said dwell point.

28. The method according to claim 26, wherein said device further comprises at least one fiducial marker utilized to align said dwell point with said locus of neoplastic disease.

29. A method of making the device according to claim 1, said method comprising:
    (a) creating a cast of said body cavity of said subject;
    (b) scanning said cast in three dimensions;
    (c) printing a planning device using 3-D printing directed by coordinates acquired from said scanning, said printing including printing said imagable registration fiducials;
    (d) implanting said planning device in said body cavity of said subject;
    (e) imaging said subject with said planning device implanted in said body cavity;
    (f) computing dose and distribution of radiation; and
    (g) printing said device using 3-D printing.

30. The method according to claim 29, wherein data from said imaging is utilized to assemble a 3-dimensional model of anatomy specific to said subject corresponding to said imagable registration fiducials of said device.

31. The method according to claim 29, wherein step (f) further comprises applying a channel layout algorithm with inverse dose planning to compute said at least one curvature constrained channel.

32. The method according to claim 29, wherein step (f) further comprises applying said channel layout algorithm with inverse dose planning to compute at least one said dwell point for said at least one local means of tumor control.

33. The method according to claim 29, wherein step (g) further comprises printing said shielding material.

34. The method according to claim 29, wherein step (g) further comprises printing said imagable registration fiducials.

35. The method according to claim 29, wherein step (g) further comprises printing said at least one local means of tumor control.

36. The method according to claim 29, wherein said local means of tumor control is a source of ionizing radiation.

* * * * *